United States Patent
Shelton, IV et al.

(10) Patent No.: US 11,399,928 B2
(45) Date of Patent: Aug. 2, 2022

(54) LINKING ELEMENTS FOR IMPLANTABLE SPHINCTER ASSISTANCE DEVICE

(71) Applicant: ETHICON LLC, Guaynabo, PR (US)

(72) Inventors: Frederick E. Shelton, IV, Hillsboro, OH (US); Kevin M. Fiebig, Cincinnati, OH (US); Jerome R. Morgan, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 860 days.

(21) Appl. No.: 16/224,883

(22) Filed: Dec. 19, 2018

(65) Prior Publication Data
US 2020/0197154 A1 Jun. 25, 2020

(51) Int. Cl.
| | | |
|---|---|---|
| *A61F 2/04* | (2013.01) | |
| *A61B 17/12* | (2006.01) | |
| *A61F 2/00* | (2006.01) | |
| *A61B 17/00* | (2006.01) | |
| *A61B 18/00* | (2006.01) | |

(52) U.S. Cl.
CPC .......... *A61F 2/04* (2013.01); *A61B 17/12099* (2013.01); *A61F 2/0004* (2013.01); *A61B 17/12009* (2013.01); *A61B 2017/00818* (2013.01); *A61B 2017/00827* (2013.01); *A61B 2017/00876* (2013.01);
(Continued)

(58) Field of Classification Search
CPC ........ A61B 17/12009; A61B 17/12099; A61B 17/12022; A61B 17/12013; A61B 17/12018; A61B 2017/00818; A61B 2017/00827; A61B 2017/00876; A61B 2018/00553; A61F 2/0004; A61F 2/04; A61F 2002/044; A61F 2210/009; A44C 13/00; A63H 33/062; Y10T 29/49591
See application file for complete search history.

(56) References Cited

U.S. PATENT DOCUMENTS

| | | | |
|---|---|---|---|
| 5,122,136 A | 6/1992 | Guglielmi et al. | |
| 5,204,382 A | 4/1993 | Wallace et al. | |

(Continued)

FOREIGN PATENT DOCUMENTS

| | | |
|---|---|---|
| DE | 3011742 A1 | 10/1981 |
| EP | 1547549 A2 | 6/2005 |

(Continued)

OTHER PUBLICATIONS

U.S. Appl. No. 15/908,875, entitled Laparoscopic Sizing Instrument, filed Mar. 3, 2018.
(Continued)

*Primary Examiner* — Jocelin C Tanner
(74) *Attorney, Agent, or Firm* — Frost Brown Todd LLC

(57) ABSTRACT

An implantable restriction device includes a plurality of beads, a plurality of links joining the beads together, and a parking feature. Each bead in the plurality of beads includes a housing, a passageway extending through the housing, and at least one magnet disposed around the passageway. The plurality of links are slidably disposed in corresponding passageways of the beads such that the plurality of beads can transition between a constricted configuration and an expanded configuration. The parking feature can consistently position the at least one link relative to the housing in the contracted configuration.

20 Claims, 21 Drawing Sheets

(52) U.S. Cl.
CPC ............... *A61B 2018/00553* (2013.01); *A61F 2002/044* (2013.01); *A61F 2210/009* (2013.01)

(56) References Cited

U.S. PATENT DOCUMENTS

| | | |
|---|---|---|
| 5,509,888 A | 4/1996 | Miller |
| 5,592,835 A * | 1/1997 | Herr ..................... A44C 11/007 63/21 |
| 5,702,361 A | 12/1997 | Evans, II et al. |
| 6,543,456 B1 | 4/2003 | Freeman |
| 7,175,589 B2 | 2/2007 | Deem et al. |
| 7,374,565 B2 | 5/2008 | Hassler, Jr. et al. |
| 7,390,294 B2 | 6/2008 | Hassler, Jr. |
| 7,445,010 B2 | 11/2008 | Kugler et al. |
| 7,481,763 B2 | 1/2009 | Hassler, Jr. et al. |
| 7,695,427 B2 | 4/2010 | Kugler et al. |
| 7,727,141 B2 | 6/2010 | Hassler, Jr. et al. |
| 7,879,068 B2 | 2/2011 | Dlugos et al. |
| 8,070,670 B2 | 12/2011 | Deem et al. |
| 8,603,023 B2 | 12/2013 | Albrecht et al. |
| 8,617,049 B2 | 12/2013 | Dlugos, Jr. et al. |
| 8,636,751 B2 | 1/2014 | Albrecht et al. |
| 8,715,157 B2 | 5/2014 | Berg et al. |
| 8,734,475 B2 | 5/2014 | Ekvall et al. |
| 8,870,742 B2 | 10/2014 | Dlugos, Jr. et al. |
| 8,876,761 B2 | 11/2014 | Albrecht et al. |
| 10,405,865 B2 | 9/2019 | Shelton, IV et al. |
| 10,842,496 B2 * | 11/2020 | Shelton, IV ............... A61F 2/04 |
| 2005/0283235 A1 * | 12/2005 | Kugler ............ A61B 17/12013 623/14.13 |
| 2009/0062824 A1 * | 3/2009 | Berg ..................... A61F 5/005 606/157 |
| 2011/0098731 A1 * | 4/2011 | Whitbrook ............ A61F 2/0018 606/151 |
| 2013/0053874 A1 * | 2/2013 | Ekvall ............... A61B 17/12013 606/157 |
| 2014/0336696 A1 | 11/2014 | Kugler et al. |
| 2017/0055986 A1 | 3/2017 | Harris et al. |
| 2019/0029689 A1 | 1/2019 | Shelton, IV et al. |

FOREIGN PATENT DOCUMENTS

| | | |
|---|---|---|
| WO | WO 1993/015721 A | 8/1993 |
| WO | WO 1993/016658 A1 | 9/1993 |
| WO | WO 1993/019702 A1 | 10/1993 |
| WO | WO 1997/033632 A2 | 9/1997 |
| WO | WO 1998/044965 A1 | 10/1998 |
| WO | WO 2000/054835 A1 | 9/2000 |
| WO | WO 2001/047431 A2 | 4/2001 |

OTHER PUBLICATIONS

U.S. Appl. No. 15/914,381, entitled "Tunable Magnetic Sphincter Augmentation Device," filed Mar. 7, 2018.
U.S. Appl. No. 15/914,407, entitled "MRI Compatible Magnetic Sphincter Augmentation Device," filed Mar. 7, 2018.

* cited by examiner

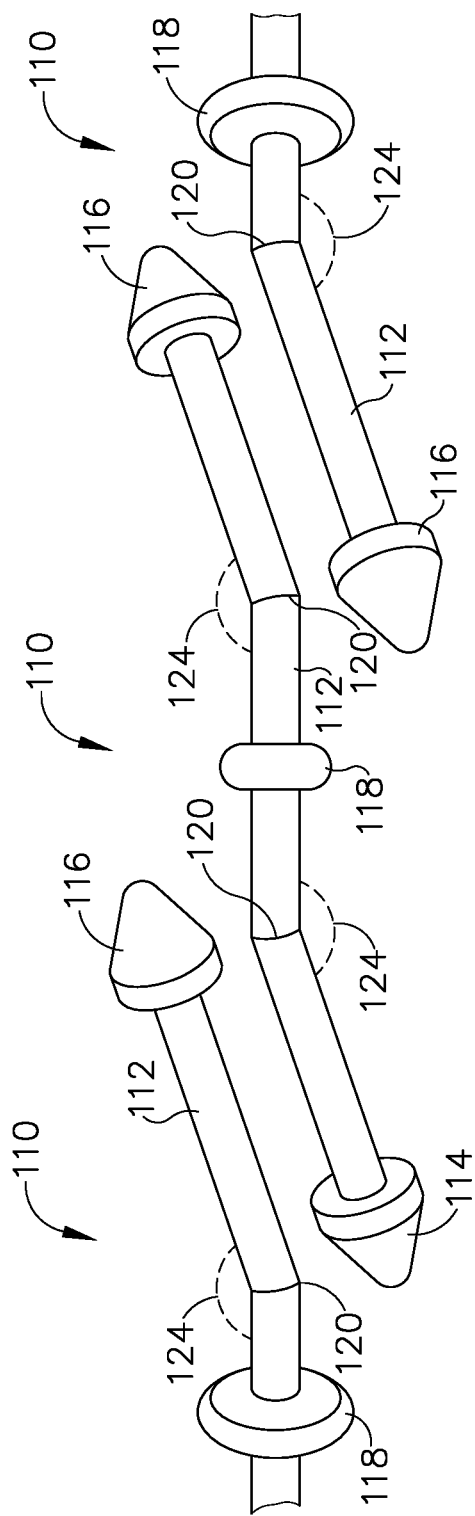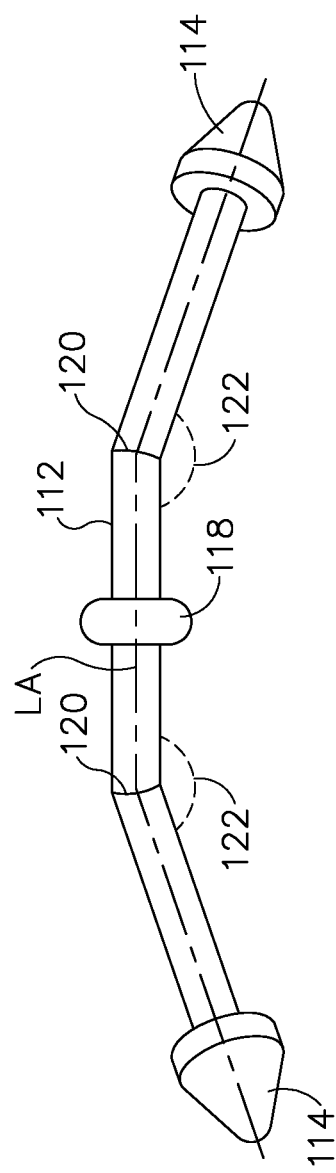
Fig.9
Fig.10

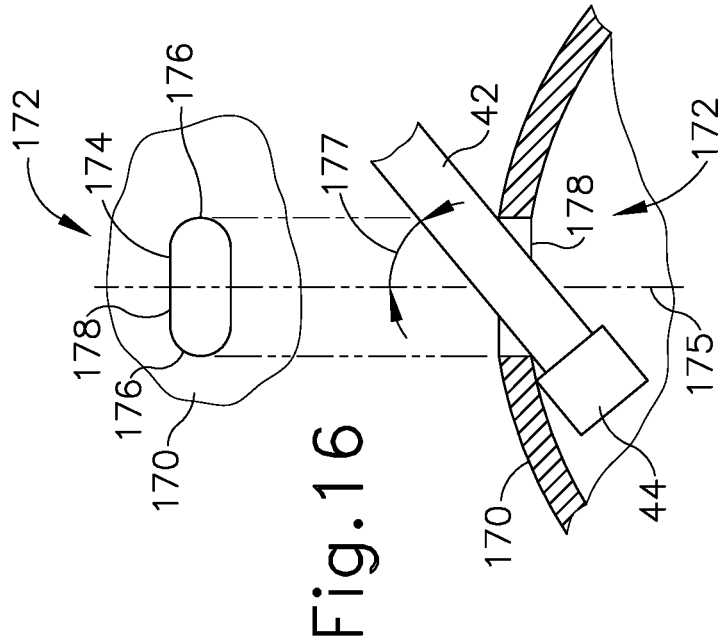
Fig.16
Fig.17
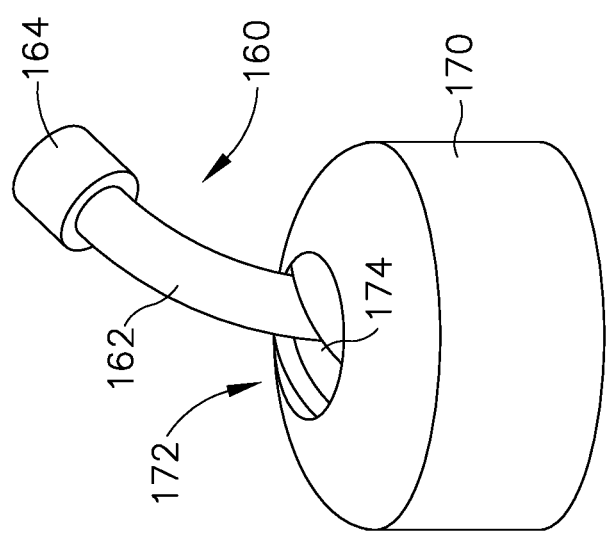
Fig.15

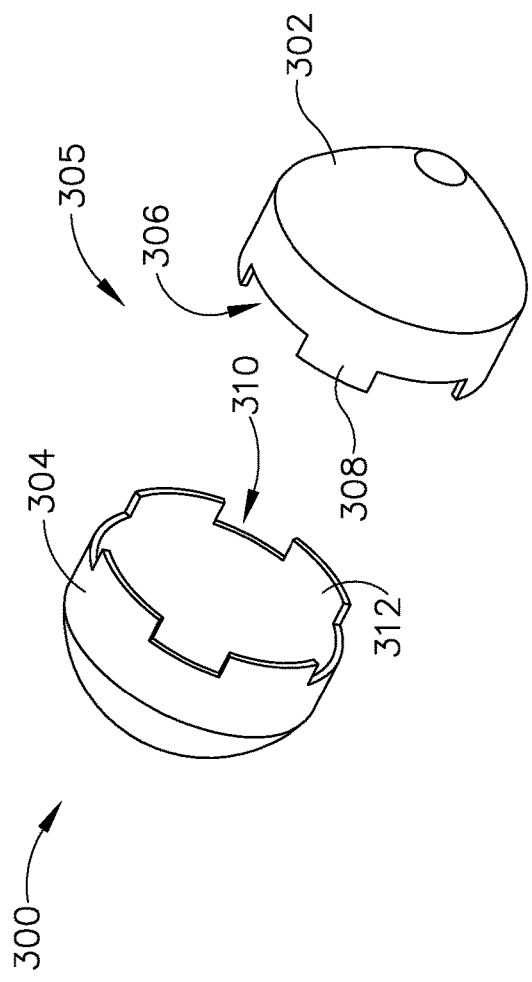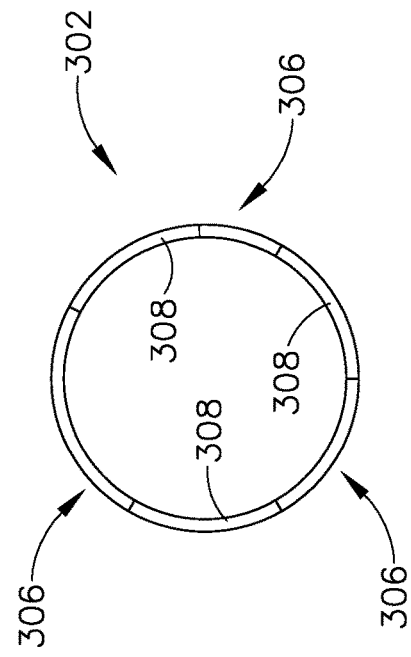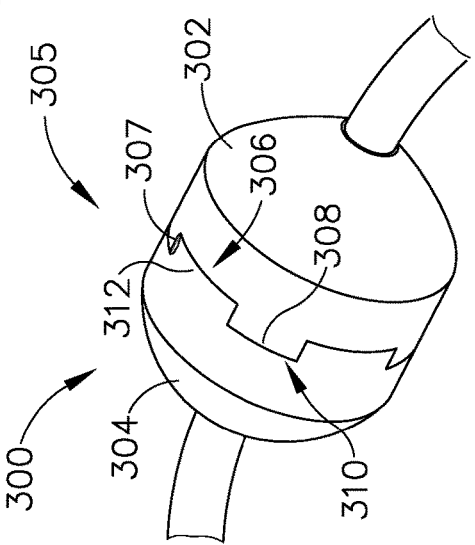

LINKING ELEMENTS FOR IMPLANTABLE SPHINCTER ASSISTANCE DEVICE

BACKGROUND

In some instances, it may be desirable to place a medical implant within or surrounding a biological lumen/passageway in order to improve or assist the function of, or otherwise affect, the biological lumen/passageway. Examples of such biological lumens/passageways include, but are not limited to, the esophagus, a fallopian tube, a urethra, or a blood vessel. Some biological passages normally function by expanding and contracting actively or passively to regulate the flow of solids, liquids, gasses, or a combination thereof. The ability of a biological passage to expand and contract may be compromised by defects or disease. One merely illustrative example of a condition associated with decreased functionality of a body passage is Gastro Esophageal Reflux Disease ("GERD"), which effects the esophagus.

A normal, heathy, esophagus is a muscular tube that carries food from the mouth, through the chest cavity and into the upper part of the stomach. A small-valved opening in the esophagus, called the lower esophageal sphincter ("LES"), regulates the passage of food from the esophagus into the stomach, as well as the passage of acidic fluids and food from the stomach toward the esophagus. The LES may also regulate stomach intra-gastric pressures. A healthy LES may contain pressure of gasses within the stomach at around 10 mm Hg greater than normal intragastrical pressure, thereby impeding acidic gases/fluids from refluxing from the stomach back into the esophagus. When functioning properly, a pressure difference greater than 10 mm Hg may regulate when the LES opens to allow gasses to be vented from the stomach toward the esophagus.

If the LES relaxes, atrophies, or degrades for any reason, the LES may cease functioning properly. Therefore, the LES may fail to sufficiently contain pressure of gasses within the stomach such that acidic contents of the stomach may travel back into the esophagus, resulting in reflux symptoms. Two primary components that control the LES are the intrinsic smooth muscle of the distal esophagus wall and the skeletal muscle of the crural diaphragm or esophageal hiatus. A causation of esophageal reflux, which may be associated with GERD, is relaxation of one or both of the smooth muscle of the distal esophagus wall or the hiatal diaphragm sphincter mechanisms. Chronic or excessive acid reflux exposure may cause esophageal damage. Conventionally, treatment for GERD may involve either open or endoscopic surgical procedures. Some procedures may include a fundoplication that mobilizes of the stomach relative to the lower esophagus, or suturing a pleat of tissue between the LES and the stomach to make the lower esophagus tighter.

Examples of devices and methods that have been developed to treat anatomical lumens by providing sphincter augmentation are described in U.S. Pat. No. 7,175,589, entitled "Methods and Devices for Luminal and Sphincter Augmentation," issued Feb. 13, 2007, the disclosure of which is incorporated by reference herein; U.S. Pat. No. 7,695,427, entitled "Methods and Apparatus for Treating Body Tissue Sphincters and the Like," issued Apr. 13, 2010, the disclosure of which is incorporated by reference herein; U.S. Pat. No. 8,070,670, entitled "Methods and Devices for Luminal and Sphincter Augmentation," issued Dec. 6, 2011, the disclosure of which is incorporated by reference herein; and U.S. Pat. No. 8,734,475, entitled "Medical Implant with Floating Magnets," issued May 27, 2014, the disclosure of which is incorporated by reference herein.

While various kinds and types of instruments have been made and used to treat or otherwise engage anatomical lumens, it is believed that no one prior to the inventors has made or used an invention as described herein.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 9 depicts an elevational side view of an alternative array of links that may be readily incorporated into the sphincter augmentation device of FIG. 3;

FIG. 10 depicts an elevational top view of an individual link of the array of links of FIG. 9;

FIG. 15 depicts a perspective view of an alternative bead housing coupled with the link of FIG. 14;

FIG. 16 depicts a top plan view of a portion of the bead housing of FIG. 15;

FIG. 17 depicts a cross-sectional side view of a portion of the bead housing and link of FIG. 15;

FIG. 31 depicts an exploded perspective view of an alternative bead that may be readily incorporated into the sphincter augmentation device of FIG. 3;

FIG. 32 depicts a perspective view of the bead of FIG. 31;

FIG. 33 depicts an elevational front view of a housing of the bead of FIG. 31;

Figure 1:
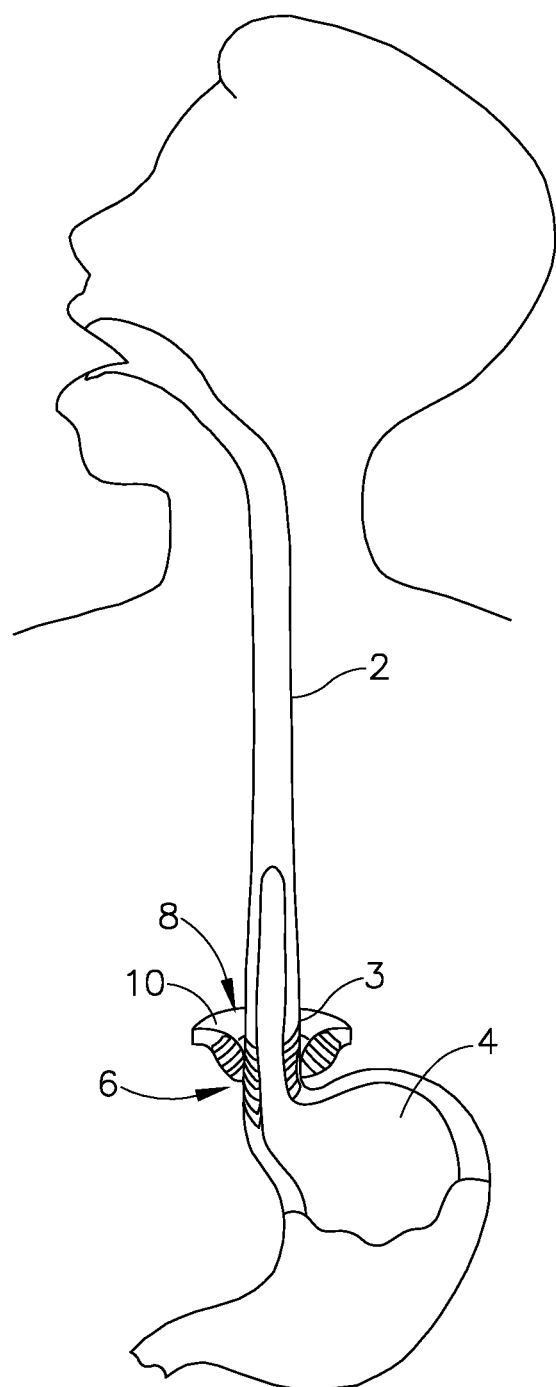
FIG. 1 depicts a cross-sectional side view, taken along a coronal plane of the body, of a biological passage.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Overview of Exemplary Sphincter Augmentation Device

Figure 2:
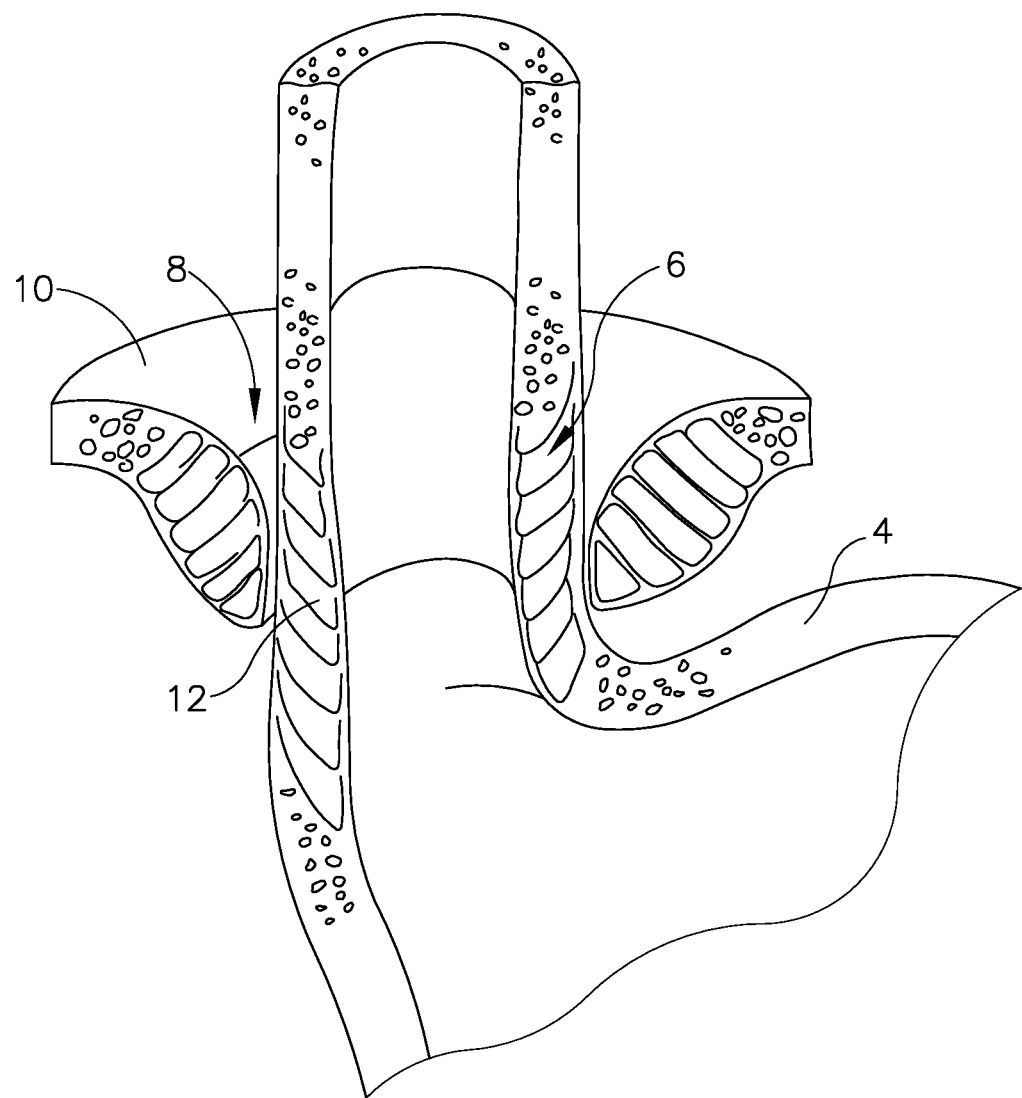
FIG. 2 depicts a cross-sectional isometric view, taken along a coronal plane of the body, of a human esophagogastric junction.
Figure 3:
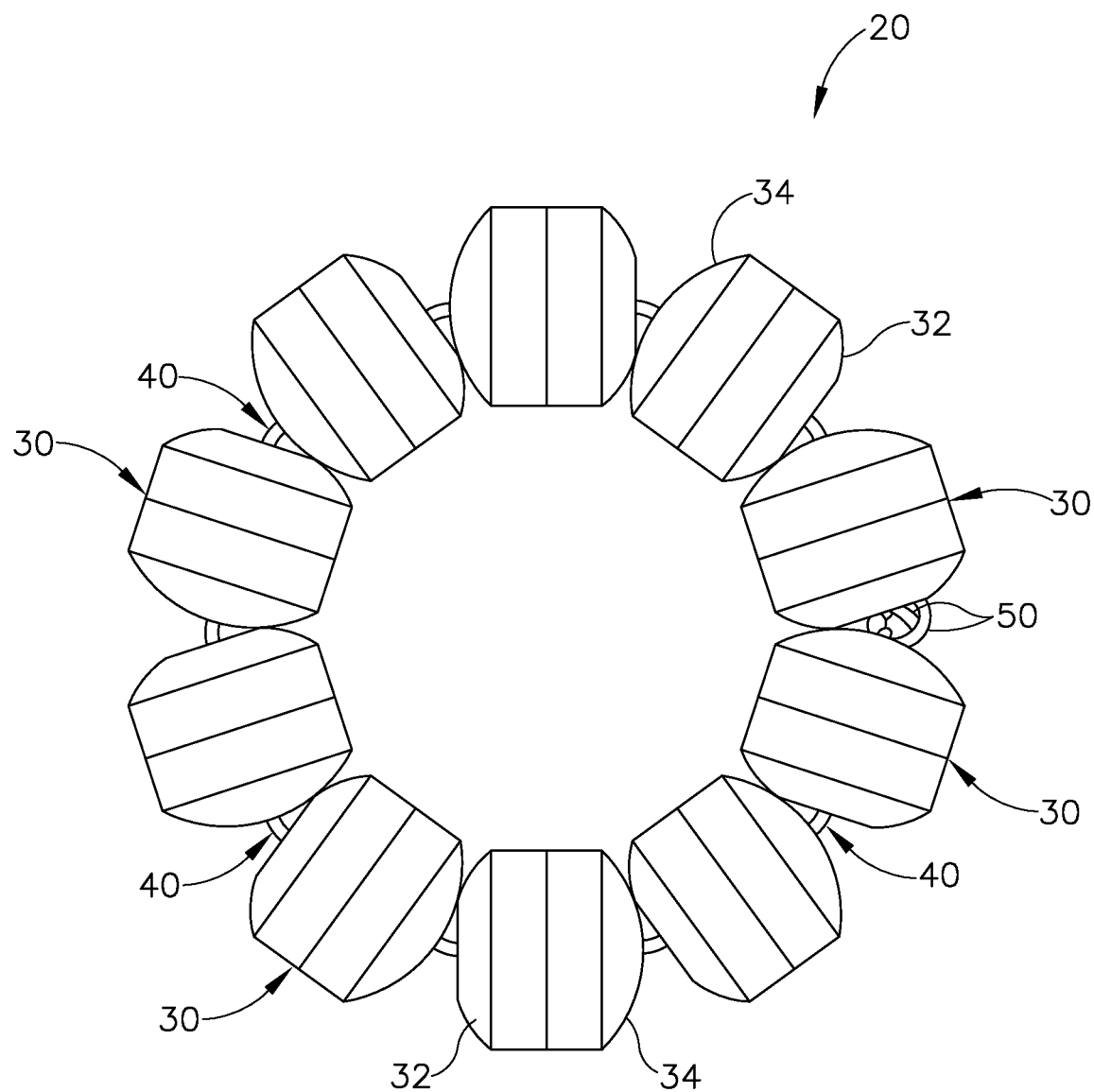
FIG. 3 depicts a top plan view of an exemplary sphincter augmentation device.

FIGS. 1-2 show selected portions of human anatomy, which includes an esophagus (2) extending from the mouth, through a hiatus (8) defined by a diaphragm (10), and into a stomach (4). Esophagus (2) also includes a distal esophagus (3) and an LES (6). LES (6) is located along distal esophagus (3) adjacent to the junction of esophagus (2) and stomach (4). The portion of LES (6) extending through hiatus (8) is supported by diaphragm (10). When functioning properly, LES (6) is configured to transition between an occluded state and an opened state (as shown in FIG. 2). As best seen in FIG. 2, LES (6) includes a plurality of sling fibers (12). Sling fibers (12) are smooth muscle tissue that may help regulate LES (6) transition between the occluded state and the open state. Hiatus (8) of diaphragm (10) may also help LES (6) transition between the occluded state and the open state.

A healthy LES (6) transitions between the occluded state and the opened state to act as a valve. In other words, a healthy LES (6) may transition from the occluded state to the opened state to allow solids, liquids, and/or gasses to selectively travel between esophagus (2) and stomach (4). For example, a healthy LES (6) may transition from the occluded state to the opened state to permit a bolus of food to travel from esophagus (2) into stomach (4) during peristalsis; or to vent intra-gastric pressure from stomach (4) toward esophagus (2). Additionally, in the occluded state, a healthy LES (6) may prevent digesting food and acidic fluid from exiting stomach (4) back into esophagus (2).

If LES (6) ceases functioning properly by prematurely relaxing, and thereby improperly transitioning esophagus (2) from the occluded state to the opened state, undesirable consequences may occur. Examples of such undesirable consequences may include acidic reflux from stomach (4) into esophagus (2), esophageal damage, inflamed or ulcerated mucosa, hiatal hernias, other GERD symptoms, or other undesirable consequences as will be apparent to one having ordinary skill in the art in view of the teachings herein. Therefore, if an individual has an LES (6) that prematurely relaxes, causing improper transitions from the occluded state to the opened state, it may be desirable to insert an implant around a malfunctioning LES (6) such that the implant and/or LES (6) may properly transition between the occluded state and the opened state.

Figure 4:
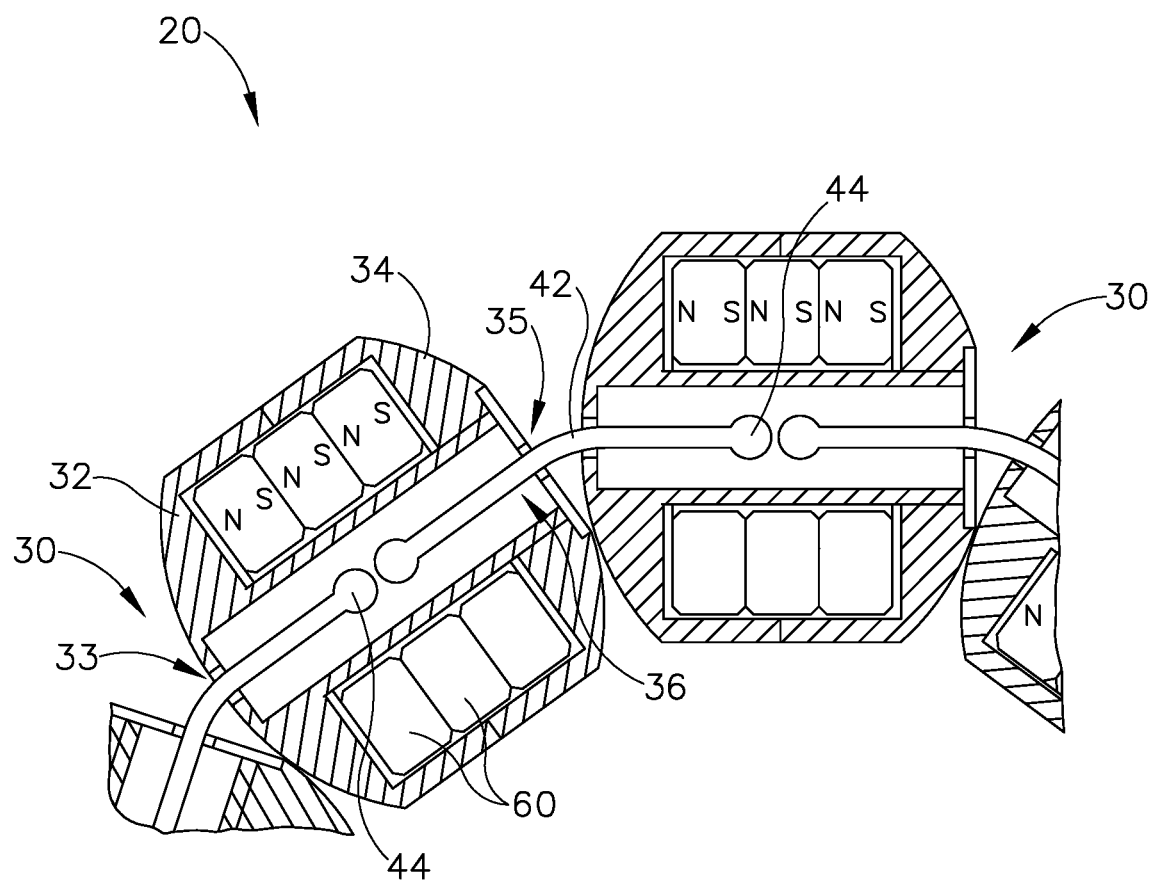
FIG. 4 depicts a partial, cross-sectional view of a portion of the sphincter augmentation device of FIG. 3.

FIGS. 3-5B show an exemplary sphincter augmentation device (20) that may be used as an implant around a malfunctioning LES (6) to assist the LES (6) in transitioning between the occluded state and the opened state. Device (20) of this example comprises a plurality of beads (30) that are joined together by a plurality of links (40). Each bead (30) comprises a pair of housings (32, 34) that are securely fastened to each other. By way of example only, housings (32, 34) may be formed of a non-ferrous material (e.g., titanium, plastic, etc.). Each bead (30) further comprises a plurality of annular or toroidal rare-earth permanent magnets (60) that are stacked next to each other within housings (32, 34). In the present example, magnets (60) are completely sealed within beads (30). As best seen in FIG. 4, each bead (30) also defines a chamber (36) that is configured to receive a portion of a respective pair of links (40). Housing (32) defines an opening (33) at one end of chamber (36); while housing (34) defines an opening (35) at the other end of chamber (36).

Each link (40) of the present example comprises a wire (42) that is pre-bent to form an obtuse angle. The free end of each wire (42) terminates in a ball tip (44). Beads (30) are joined together by links (40) such that a first end portion of a link (40) is in one bead (30), a second end portion of the same link (40) is in another bead (30), and an intermediate portion of the same link (40) is positioned between those two beads (30). Chambers (36) of beads (30) are configured to freely receive ball tips (44) and adjacent regions of wires (42); while openings (33, 35) are configured to prevent ball tips (44) from exiting chambers (36). Openings (33, 35) are nevertheless sized to allow wire (42) to slide through openings (33, 35). Thus, links (40) and beads (30) are configured to allow beads (30) to slide along links (40) through a restricted range of motion.

Figure 5A:
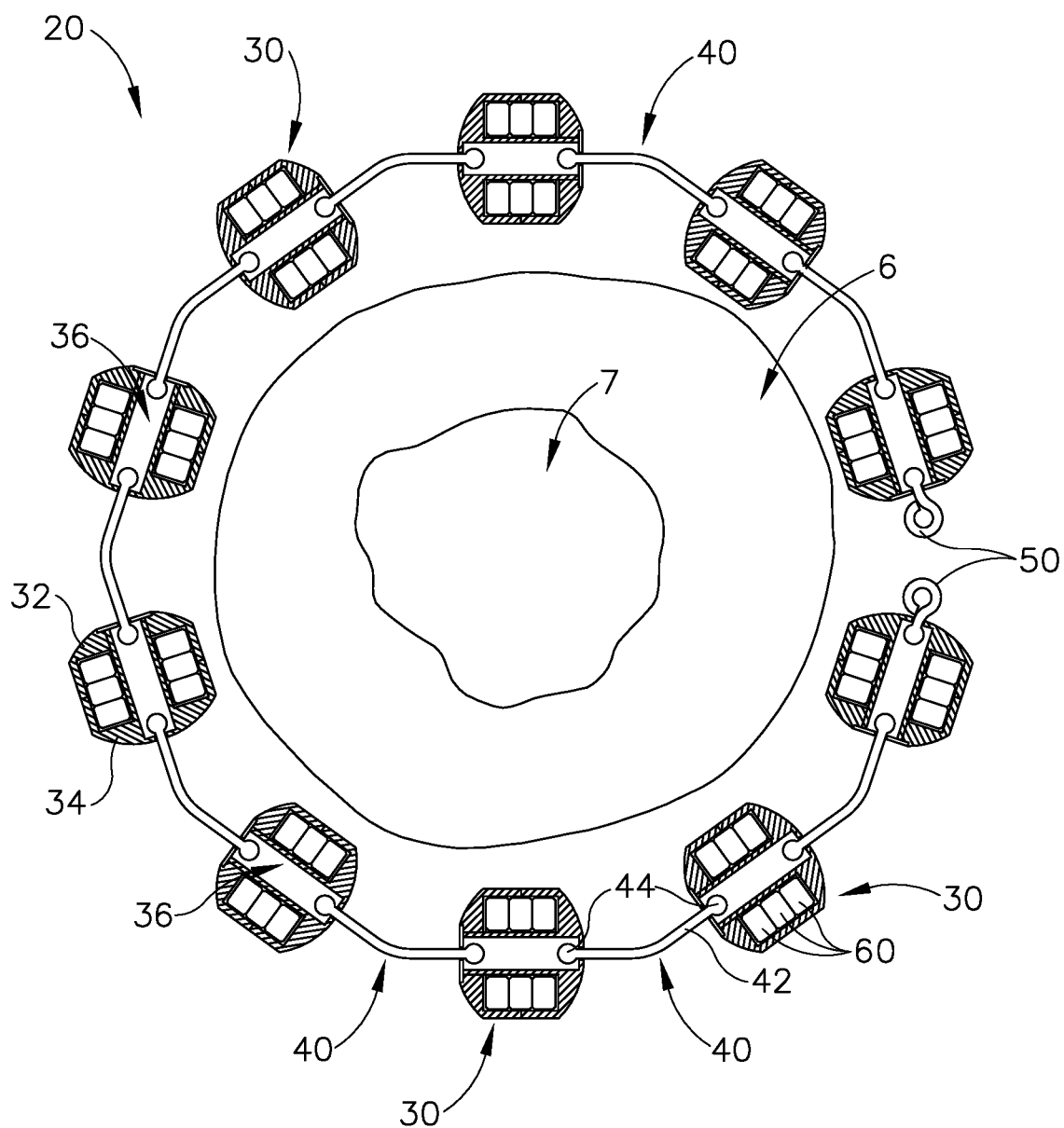
FIG. 5A depicts a top, cross-sectional view of the sphincter augmentation device of FIG. 3 positioned about an LES, with the sphincter augmentation device in an open and expanded configuration.
Figure 5B:
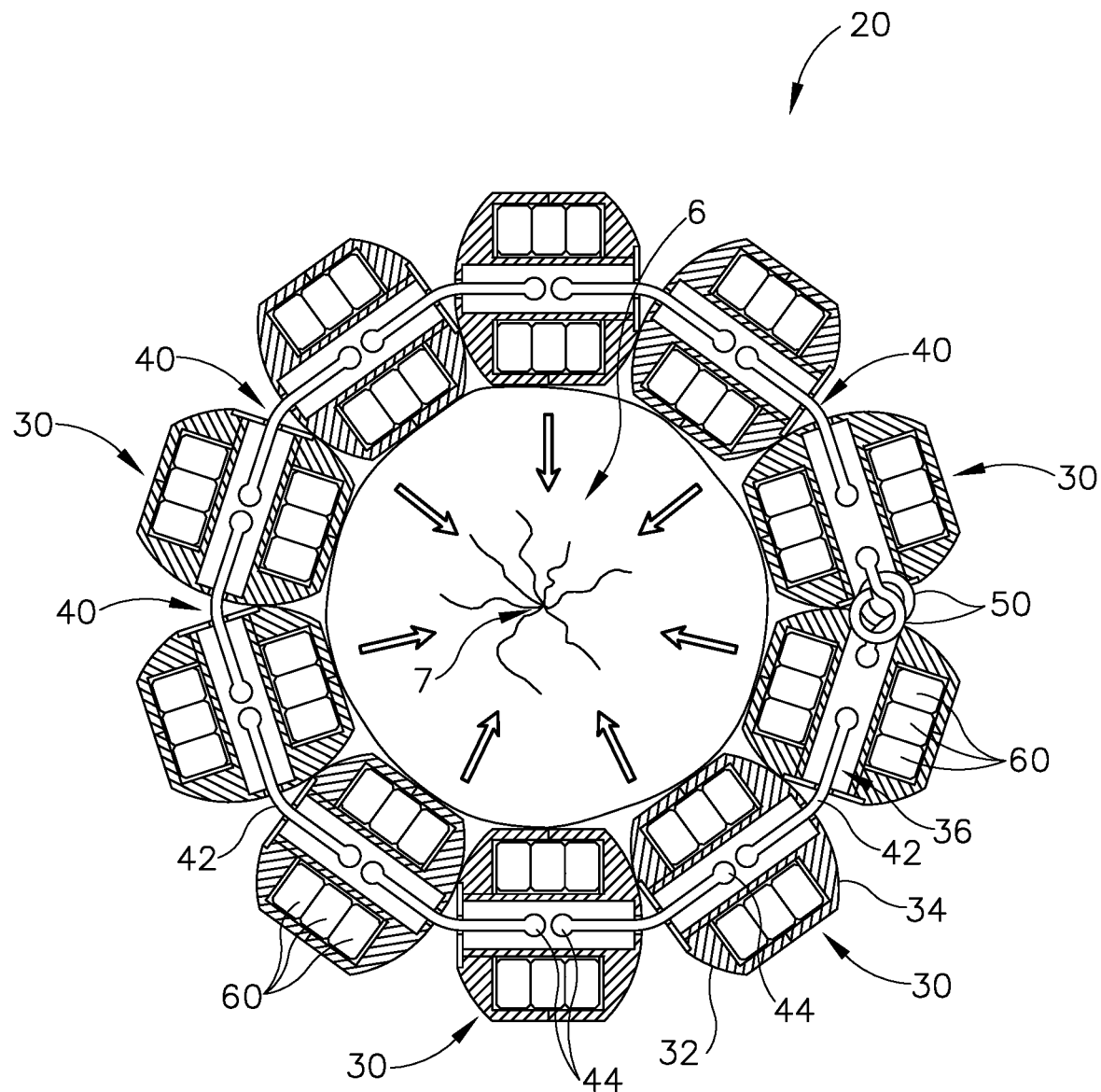
FIG. 5B depicts a top, cross-sectional view of the sphincter augmentation device of FIG. 3 positioned about the LES of FIG. 5A, with the sphincter augmentation device in a closed and contracted configuration.

As best seen in FIGS. 5A-5B, two beads (30) have opposing fastener features (50) that allow the ends of device (20) to be coupled together to form a loop. In the present example, fastener features (50) comprise eyelets. In some other versions, fastener features (50) comprise complementary clasp features. As another merely illustrative example, fastener features (50) may be configured and operable in accordance with one or more of the teachings of U.S. patent application Ser. No. 15/664,665, entitled "Method for Assisting a Sphincter," filed Jul. 31, 2017, issued as U.S. Pat. No. 10,405,865 on Sep. 10, 2019, the disclosure of which is incorporated by reference herein. Other suitable ways in which the ends of device (20) may be coupled together to form a loop will be apparent to those of ordinary skill in the art in view of the teachings herein. Those of ordinary skill in the art will also recognize that it may be desirable to provide fastener features (50) that can be decoupled if it becomes necessary or otherwise warranted to remove device (20) from the patient.

FIG. 5A shows device (20) in an open, expanded state, with device (20) being positioned about LES (6). At this stage, the opening (7) defined by LES (6) is in a persistently open state (e.g., allowing the patient to undesirably experience GERD and/or other undesirable conditions), warranting the securement of device (20) about the LES (6). FIG. 5B shows device (20) secured about the LES (6), with device (20) in a closed, contracted state. Device (20) is secured closed via fastener features (50). Magnets (60) are oriented within beads (30) such that each bead (30) will be magnetically attracted to the adjacent bead (30) in device (20). In other words, beads (30) are magnetically attracted to each other to magnetically bias device (20) toward the contracted configuration shown in FIG. 5B.

With device (20) secured around the LES (6) and in the contracted configuration, device (20) deforms the LES (6) radially inwardly to substantially close the opening defined by the LES (6). In doing so, device (20) prevents the patient from experiencing GERD and/or other undesirable conditions that may be associated with a persistently open opening (7) at the LES (6). While magnets (60) have a tesla value that is high enough to substantially maintain opening (7) in a closed state to the point of preventing GERD and/or other undesirable conditions that may be associated with a persistently open opening (7), the tesla value of magnets (60) is low enough to allow LES (6) to expand radially outwardly to accommodate passage of a bolus of food, etc. through the opening (7) of LES (6). To accommodate such expansion, beads (30) may simply slide along links (40) to enlarge the effective diameter of device (20) as the bolus passes. After the bolus passes, the magnetic bias of magnets (60) will return device (20) to the contracted state shown in FIG. 5B. Device (20) thus ultimately prevents GERD and/or other undesirable conditions that may be associated with a persistently open opening (7); while still permitting the normal passage of food, etc. from the esophagus (2) to the stomach (4).

In addition to the foregoing, device (20) may be constructed and operable in accordance with at least some of the teachings of U.S. Pat. No. 7,695,427, the disclosure of which is incorporated by reference herein; and/or U.S. patent application Ser. No. 15/664,665, entitled "Method for Assisting a Sphincter," filed Jul. 31, 2017, issued as U.S. Pat. No. 10,405,865 on Sep. 10, 2019, the disclosure of which is incorporated by reference herein.

II. Exemplary Sphincter Augmentation Devices with Improved Expansion and Motion Control As mentioned above, magnets (60) are oriented within beads (30) such that each bead (30) will be magnetically attracted to the adjacent bead (30) in device (20), thereby biasing device (20) toward the contracted state during exemplary use, as shown in FIG. 5B. As also shown in FIG. 5B, exterior portions of adjacent beads (30) are dimensioned to abut against each other in the contracted state, which may help define the overall structure of device (20) in the contracted state. When device (20) is suitably coupled with LES (6), the tesla value between magnets (60) may be high enough to maintain opening (7) in a closed state to the point of preventing undesirable conditions that may be associated with a persistently open opening (7), but low enough such that beads (30) may move radially outwardly relative to each other by sliding along links (40), thereby effectively expanding device (20) to accommodate passage of a bolus of food, etc. through opening (7) of LES (6). Therefore, device (20) may repeatedly transition between the contracted state and an expanded state while suitably attached to LES (6).

A. Features for Improved Motion between Links and Beads

If beads (30) are somehow obstructed from sliding along links (40), or if links (40) are somehow obstructed from moving relative to each other, device (20) may be prevented from suitably transitioning between the contracted state and the expanded state. For instance, if two links (40) having ball tips (44) located in the same chamber (36) somehow manage to tangle with each other, interfere with each other, or otherwise become undesirably coupled with each other, bead (30) sharing links (40) may be prevented from suitably sliding along links (40), which may in turn prevent device (20) from suitably transitioning between the contracted state and the expanded state in accordance with the description above. As another example, a link (40) may become snagged or otherwise undesirably fixed relative to a coupled bead (30) via interaction between wire (42) and opening (33, 35), which may also prevent bead (30) from suitably sliding along link (40), which may in turn prevent device (20) from suitably transitioning between the contracted state and the expanded state in accordance with the description above. Therefore, it may be desirable to have features that prevent links (40) from becoming entangled with each other and within openings (33, 35).

Figure 6:
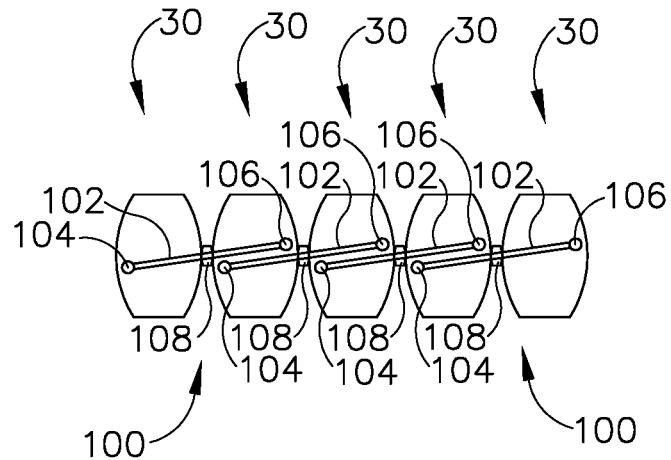
FIG. 6 depicts a top, cross-sectional view of an array of beads of the sphincter augmentation device of FIG. 3, connected to each other by alternative exemplary links, where the beads and links are in a contracted configuration.
Figure 7:
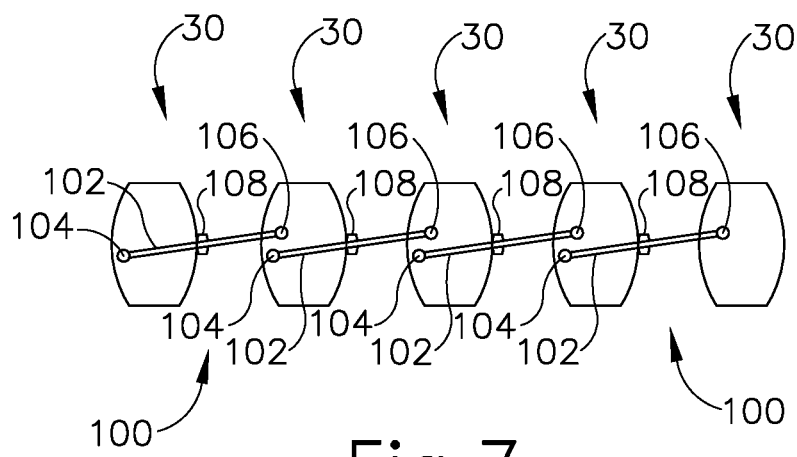
FIG. 7 depicts a top, cross-sectional view of the array of beads and links of FIG. 6, where the beads and links are in a partially expanded configuration.
Figure 8:
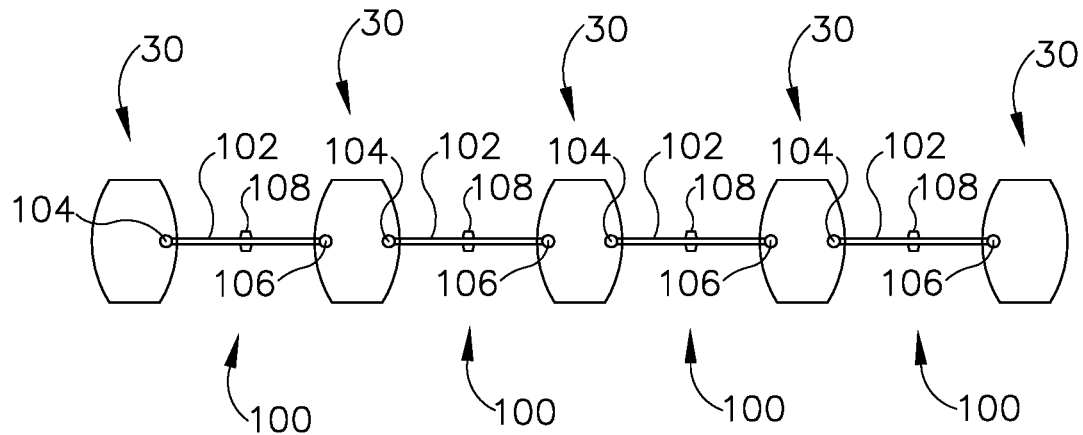
FIG. 8 depicts a top, cross-sectional view of the array of beads and links of FIG. 6, where the beads and links are in a fully expanded configuration.

FIGS. 6-8 show a plurality of beads (30) connected to each other by exemplary alternative links (100) in replacement of links (40) described above in order to form device (20). As will be described in greater detail below, links (100) include a spacer bead (108) configured to selectively abut against exterior surfaces of beads (30) in order to align links (100) relative to adjacent links (100) to help prevent unwanted interference between each other.

While not explicitly shown in FIGS. 6-8, beads (30) house magnets (60) such that beads (30) are magnetically attracted to adjacent beads (30). Links (100) are substantially similar to links (40) described above, with differences elaborated below. Therefore, links (100) include a wire (102) that terminate into ball tips (104, 106) on opposite ends. While FIGS. 6-8 show links (100) viewed from the side, wires (102) may include an obtuse angle when viewed from above, similar to wires (42) viewed from above as shown in FIG. 5B. Alternatively, wires (102) may include any suitable combination of bends as described below.

Beads (30) are joined together by links (100) such that ball tip (104) of link (100) is in one bead (30), ball tip (106) of the same link (100) is in another bead (30), and spacer bead (108) of the same link is positioned between those two beads (30). Chambers (36) of beads (30) are configured to freely receive ball tips (104, 106) and adjacent regions of wires (102); while openings (33, 35) are configured to prevent ball tips (104, 106) from exiting chambers (36) and prevent spacer beads (108) from entering chambers (36). Openings (33, 35) are nevertheless sized to allow wire (102) to slide through openings (33, 35). Thus, links (100) and beads (30) are configured to allow beads (30) to slide along links (100) through a restricted range of motion.

Spacer beads (108) are fixated onto wire (102). Spacer beads (108) may be made from any suitable material as would be apparent to one having ordinary skill in the art in view of the teachings herein. For example, spacer bead (108) may be formed of a non-ferrous material (e.g., titanium, plastic, etc.), a ferrous material, a magnetic material, etc. Additionally, spacer beads (108) may be fixated onto wire (102) via any suitable means as would be apparent to one having ordinary skill in the art in view of the teachings herein. For example, spacer bead (108) may be formed on wire (102), may be placed on wire (102) via a resilient clip relationship, a threaded relationship, welding, adhesives, etc., or may be unitarily formed from the same material as wire (102) or ball tips (104, 106), etc.

Spacer beads (108) include contact surfaces configured to abut against exterior surfaces of adjacent beads (30) when device (20) is in the contracted state (as shown in FIG. 6), such that wire (102) is selectively oriented relative to adjacent beads (30). In particular, spacer beads (108) of adjacent links (100) are configured to orient wires (102) such that balls tips (104, 106) of adjacent links (100) sharing the same chamber (36) of bead (30) are spaced away from each other when device (20) is in the contracted state. With balls tips (104, 106) located within the same chamber (36) being spaced away from each other, adjacent links (100) may be less likely to interfere with each other as beads (30) slide along links (100) between the contracted state and the expanded state.

In some examples, as shown in FIG. 7, spacer beads (108) may be configured to associate with the exterior surface of a specific bead (30) as the plurality of beads (30) begin to slide along link (100) to transition device (20) between the contracted state and the expanded state. In other words, in some examples, beads (30) may only slide relative to one link (100) associated with a single bead (30) between the contracted state (FIG. 6) and an intermediary state (FIG. 7) somewhere between the contracted state (FIG. 6) and expanded state (FIG. 8); while beads (30) may then slide between the intermediary state and the expanded state to disassociate with spacer beads (108). Therefore, spacer beads (108) may keep adjacent links (100) spaced away from each other through contact between spacer bead (108) and the exterior surface of one bead (30) as device (20) transitions between the contracted state and the expanded state. This functionality may allow beads (30) to slide along links (100) as device (20) expands and contracts in order to define a more even, consistent, or predictable gap between adjacent beads (30) as device (20) expands and contracts.

Spacer beads (108) may be configured to associate with a single bead (30) between the contracted state (FIG. 6) and the intermediary state (FIG. 7) through any suitably means as would be apparent to one having ordinary skill in the art in view of the teachings herein. For example, spacer beads (108) may be slightly magnetized to associate with one magnetic polarity over another magnetic polarity, thereby slightly biasing spacer beads (108) to one magnetic bead (30) over another magnet magnetic bead (30).

FIGS. 9-10 show an alternative link (110) that may be readily incorporated into device (20) in replacement of link (40, 100) described above. Link (110) may be substantially similar to link (40, 100) with differences elaborated below. Therefore, link (110) includes a wire (112) and ball tips (114, 116), which are substantially similar to wire (42, 102) and ball tips (44, 104, 106) described above, with differences elaborated below. Link (110) also includes a spacer bead (118) which may be substantially similar to spacer bead (108) described above. Therefore, link (110) may be used to suitably couple beads (30) described above such that beads (30) may slide along links (110) between a contracted state and an expanded state in accordance with the description above. Additionally, spacer beads (118) may contact the exterior surfaces of beads (30) to orient wires (112) of adjacent links (110) such that ball tips (114, 116) located in the same chamber (36) do not interfere with each other.

While wire (42) of link (40) described above only has one pre-bent obtuse angle when viewed from above, as shown in FIG. 5B, wire (112) of link (110), as shown in FIG. 10, includes two bends (120) on opposite sides of spacer bead (118), where each bend (120) defines a first angle (122) to form a circular orientation when viewed from above. As shown in FIG. 10, first angles (122) of each bend (120) in a single link (110) are oriented relative to each other to promote opposite tips (114, 116) to point in the same direction when viewed from above. In other words, ball tips (114, 116) of a single link (110) both point downward when viewed from the perspective shown in FIG. 10. The circular orientation of wire (112) formed from first angle (122) of each bend (120) may help promote movement of beads (30) relative to links (40) such that device (20) expands and contracts in a radial fashion.

Additionally, as shown in FIG. 9, each bend (120) defines a second angle (124) when viewed from the side. Second angles (124) of each bend (120) of link (110) are oriented such that opposite tips (114, 116) of individual links (110) extend in the opposite direction when viewed from the side. Therefore, when links (110) are attached to beads (30), in similar fashion to links (100) described above, balls tips (114, 116) located within the same chamber (36) may be sufficiently spaced away from each other. Due to bends (120), adjacent links (110) may be less likely to interfere with each other as beads (30) slide along links (110) between the contracted state and the expanded state in accordance with the description herein.

Figure 11:
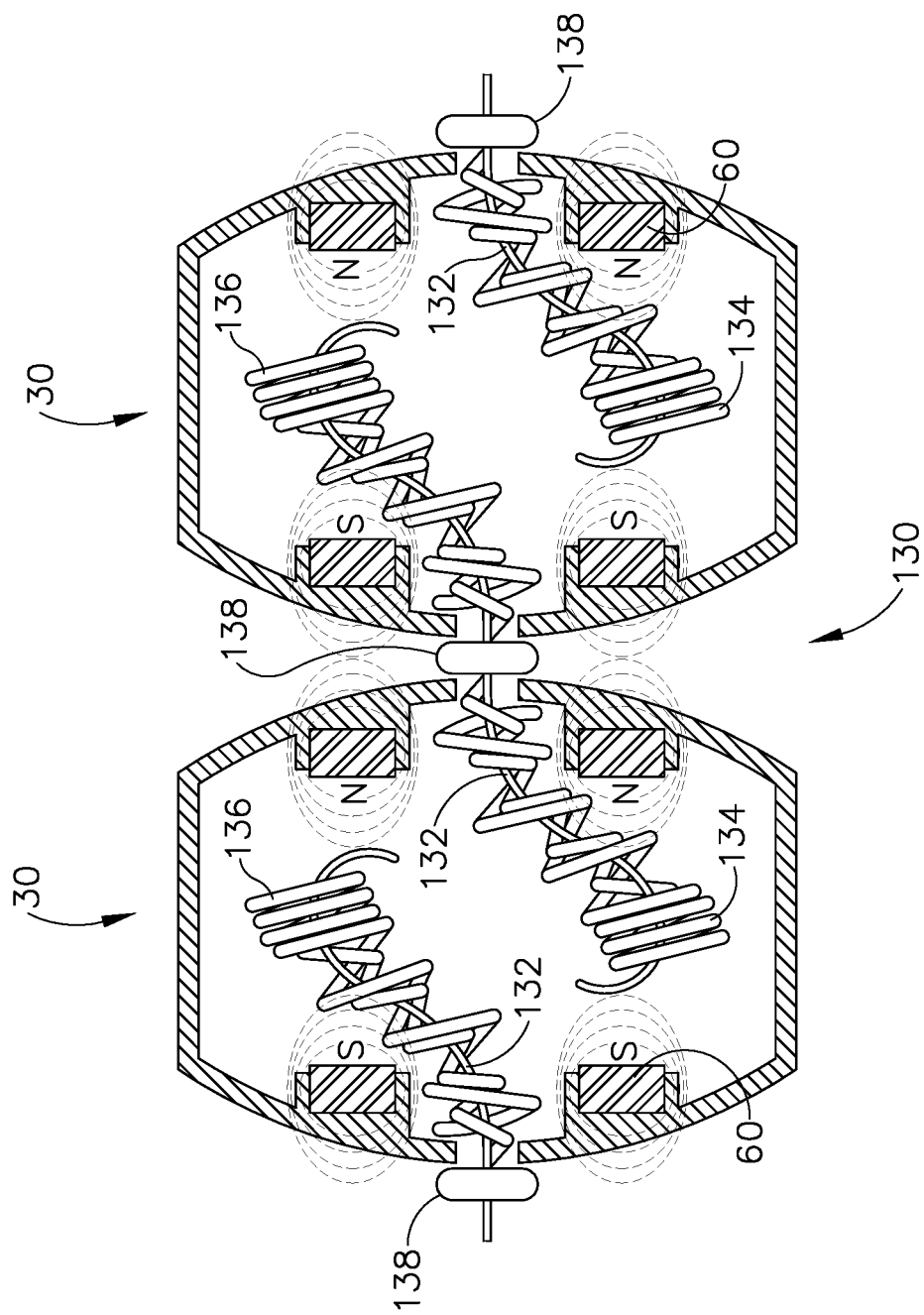
FIG. 11 depicts a top, cross-sectional view of the array of beads of FIG. 6, where the beads are connected to each other with an alternative link, where the beads and links are in a contracted configuration.

FIG. 11 show an alternative link (130) that may be readily incorporated into device (20) in replacement of link (40, 100, 110) described above. Link (130) may be substantially similar to link (40, 100, 110) with differences elaborated below. Therefore, link (130) includes a wire (132) and ball tips (134, 136), which are substantially similar to wire (42, 102, 112) and ball tips (44, 104, 106, 114, 116) described above, with differences elaborated below. Link (130) also includes a spacer bead (138) which may be substantially similar to spacer bead (108, 118) described above. Therefore, link (130) may be used to suitably couple beads (30) described above such that beads (30) may slide along links (130) between a contracted state and an expanded state in accordance with the description above. Additionally, spacer beads (138) may contact the exterior surfaces of beads (30) to orient wires (132) of adjacent links (130) such that ball tips (134, 136) located in the same chamber (36) do not interfere with each other.

Additionally, balls tips (134, 136) are magnetized such that ball tips (134, 136) within a shared bead (30) are attracted to magnets (60) in close range. Magnetized ball tips (134, 136) are attached to magnets (60) in the contracted state, as shown in FIG. 11, such that ball tips (134, 136) within the same bead (30) are spaced away from each other. Due to the magnetized nature of ball tips (134, 136), adjacent links (130) may be less likely to interfere with each other as beads (30) slide along links (130) between the contracted state and the expanded state in accordance with the description herein.

Figure 12:
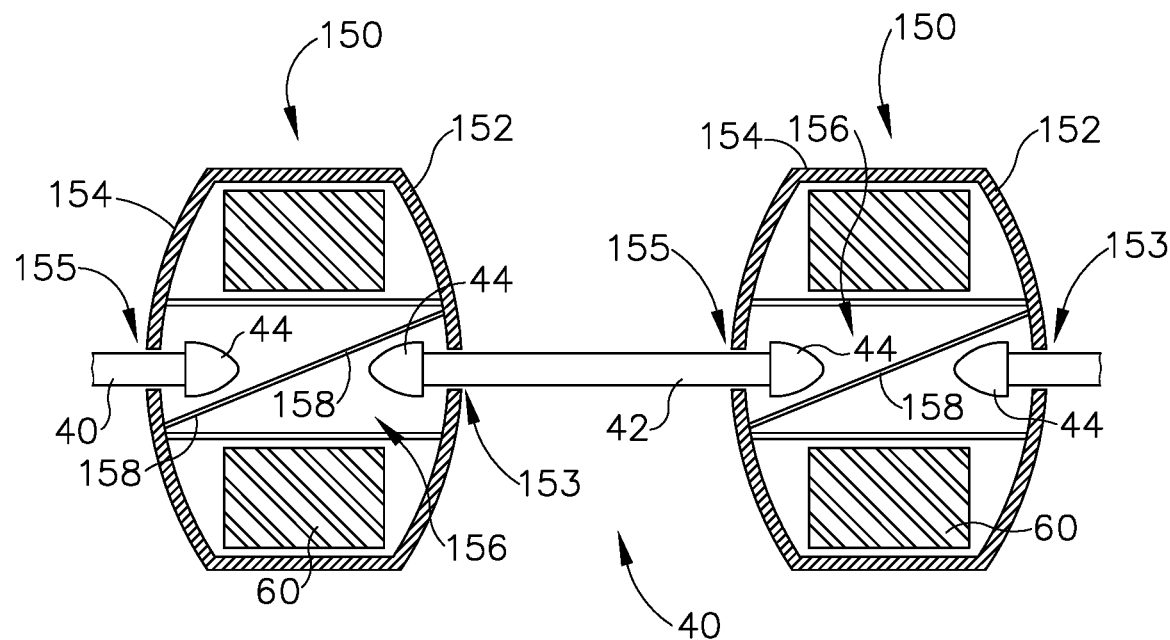
FIG. 12 depicts a side, cross-sectional view of a pair of alternative beads that may be readily incorporated into the device of FIG. 3, with the beads in the expanded configuration.
Figure 13:
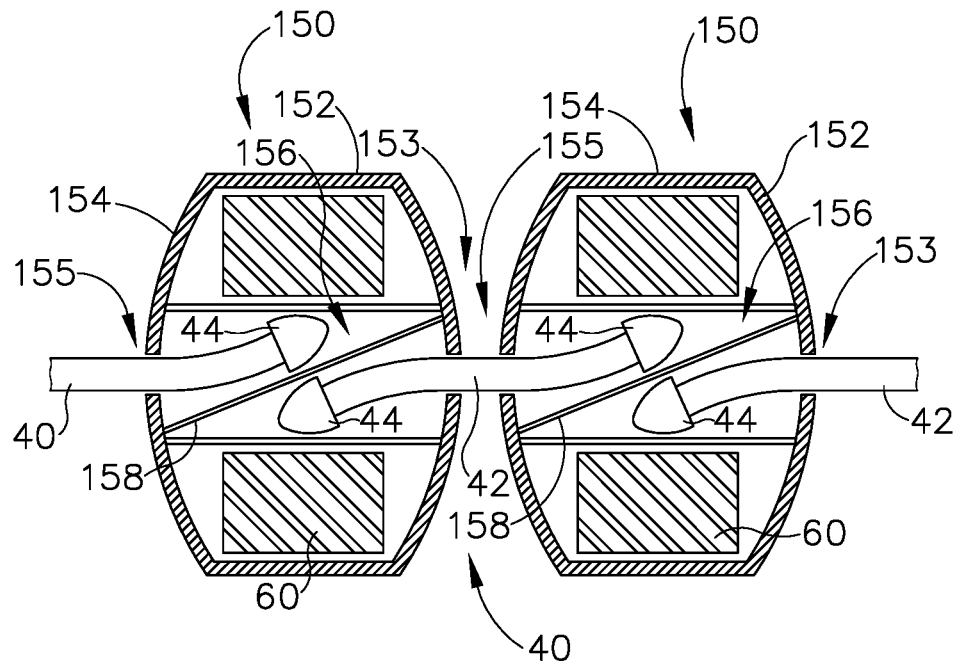
FIG. 13 depicts a side, cross-sectional view of a pair of alternative beads that may be readily incorporated into the device of FIG. 3, with the beads in the contracted configuration.

FIGS. 12-13 show an alternative bead (150) that may be readily incorporated into device (20) in replacement of bead (30) described above. Beads (150) are substantially similar to beads (30) described above with differences elaborated below. Therefore, beads (150) include housings (152, 154) defining openings (153, 155) and chamber (156); which are substantially similar to housings (32, 34), openings (33, 35) and chamber (36) described above, with differences elaborated below. Therefore, each bead (150) may suitably house at least one magnet (60). Additionally, beads (150) may be connected by links (40) such that beads (150) are configured to transition between a contracted state and an expanded state.

Unlike bead (30) described above, each bead (150) includes a partitioning layer (158) extending within chamber (156) between openings (153, 155). Partitioning layer (158) divides chamber (156) into two isolated sections, where each isolated section houses a ball tip (44) of a separate link (40). Therefore, links (40) sharing a single bead (150) are physically prevented from interacting with each other as device (20) transitions between the contracted state and the expanded state. With links (40) sharing a single bead (150) being isolated from each other, links (40) are prevented from interfering with each other as beads (150) slide along links (40) between the contracted state (FIG. 13) and the expanded state (FIG. 12) in accordance with the description herein.

Partitioning layer (158) may be formed out of any suitable material as would be apparent to one having ordinary skill in the art in view of the teachings herein. In the current example, partitioning layer (158) extends along a straight profile diagonally between openings (153, 155) such that one end of partitioning layer (158) is located above opening (153) and the other end of partitioning layer (158) is located below opening (155). However, partitioning layer (158) may extend between any suitable locations within chamber (156), and with any suitable profile as would be apparent to one having ordinary skill in the art in view of the teachings herein.

In some instances, wires (42, 102, 112, 132) may inadvertently snag, get caught in openings (33, 35, 153, 155) of beads (30, 150) such that beads (30, 150) are prevented from translating along links (40, 100, 110, 130). In other words, the geometry of wires (42, 102, 112, 132) and openings (33, 35, 153, 155) may interfere with each other such that beads (30, 150) are undesirably inhibited from translating along links (40, 100, 110, 130). This may, in turn, prevent device (20) from suitably transitioning between the contracted state and the expanded state. Therefore, it may be desirable to provide features to help prevent wires (42, 102, 112, 132) and openings (33, 35, 153, 155) from undesirably snagging with each other.

Figure 14:
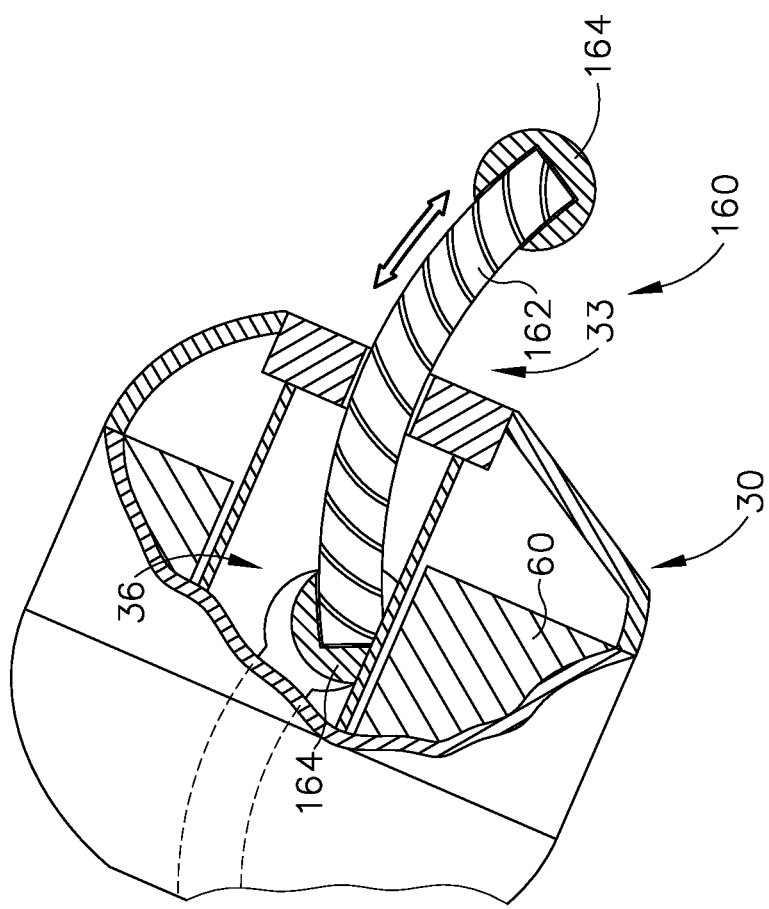
FIG. 14 depicts a side partial cross-sectional view of a bead of FIG. 6 could with an alternative link that may be readily incorporated into the sphincter augmentation device of FIG. 3.

Links (40, 100, 110, 130) are described above as having obtuse bends in wires (42, 102, 112, 132). The bend angle in wires (42, 102, 112, 132) might contribute to wires (42, 102, 112, 132) inadvertently snagging openings (33, 35, 153, 155). FIG. 14 shows an alternative link (160) that may be readily incorporated into device (20) in replacement of link (40, 100, 110, 130) described above. Link (160) may be substantially similar to link (40, 100, 110, 130) with differences elaborated below. Therefore, link (160) includes a wire (162) and ball tips (164), which are substantially similar to wire (42, 102, 112, 132) and ball tips (44, 104, 106, 114, 116, 134, 136) described above, with differences elaborated below. Therefore, link (160) may be used to suitably couple beads (30, 150) described above such that beads (30, 150) may slide along links (160) between a contracted state and an expanded state in accordance with the description above.

However, unlike wires (42, 102, 112, 132) described above, wire (162) of link (160) has an arched profile. The arched profile of wire (162) is continuous such that wire (162) does not have any "catch points" that may inadvertently snag with the profile of opening (33, 35). With the continuous arched profile of wire (162), links (60) may be prevented from undesirably snagging with beads (30), thereby allowing beads (30) to slide along links (160) between the contracted state and the expanded state in accordance with the description herein. It should be understood that while in the current example, wire (162) has a continuous arched profile, this may be modified such that the arched profile is only continuous on portions of wire (162) intended to directly interact with openings (33, 35). Therefore, portions of wire (162) that always stay within chamber (36) or always stay outside of chamber (36) may not have the arched profiled.

FIGS. 15-17 show an alternative housing (170) that may be readily incorporated into beads (30, 150) described above. Housing (170) is substantially similar to housings (32, 34, 152, 154) described above, with difference elaborated below. In particular, housing (170) defines a non-circular opening (172) dimensioned to slidably contain wire (162). Non-circular opening (172) includes two arched sections (176) connected to linear sections (178). As best seen in FIG. 17, linear sections (178) may allow wire (162) to rest against arched sections (176) to define a desired angle (177) relative to a vertical axis (175). This desired angle (177) formed by wire (162) may allow for an improved motion as device (20) transitions between the contracted state and the expanded state. The non-circular profile of opening (172)

may allow for wire (162) to pivot relative to housing (170) when in the expanded configuration to change angle (177). Additionally, linear sections (178) may provide clearance such that wire (162) does not get snagged with opening (174). Any suitable dimensions of linear section (178) and arched section (176) may be used as would be apparent to one having ordinary skill in the art in view of the teachings herein. The non-circular shape of opening (174) may allow for wire (162) to have a non-circular cross-sectional shape, such as a non-circular pattern. This may add additional control to the direction at which housing (170) forming bead can move during exemplary use. The non-circular shape of opening (174) could allow for a coil spring rather than the current design of a wire.

Figures 18, 19:
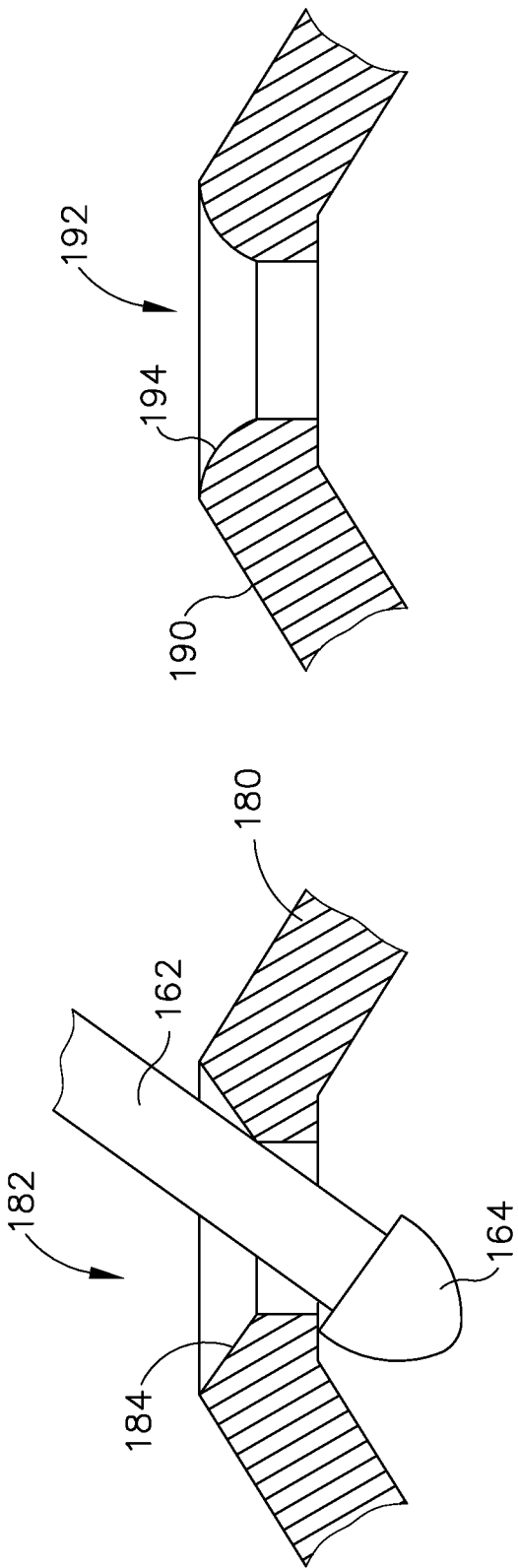
FIG. 18 depicts a cross-sectional side view of a portion of an alternative bead housing coupled with the link of FIG. 14.
FIG. 19 depicts a cross-sectional side view of a portion of an alternative bead housing.
Figure 22:
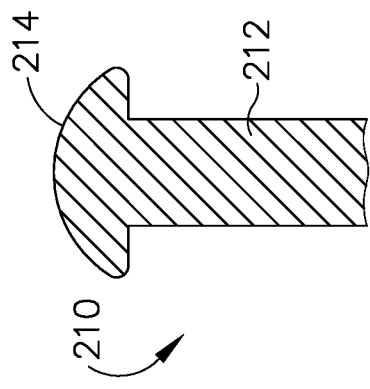
FIG. 22 depicts a cross-sectional side view of a portion of an alternative link that may be readily incorporated into the sphincter augmentation device of FIG. 3.
Figure 23:
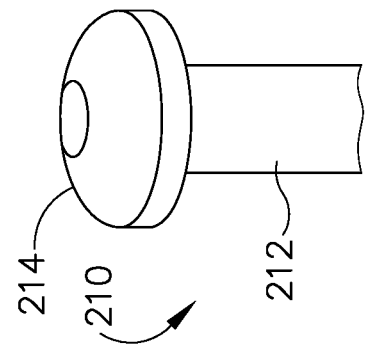
FIG. 23 depicts a perspective view of a portion of a wire of the alternative link of FIG. 22.
Figure 20:
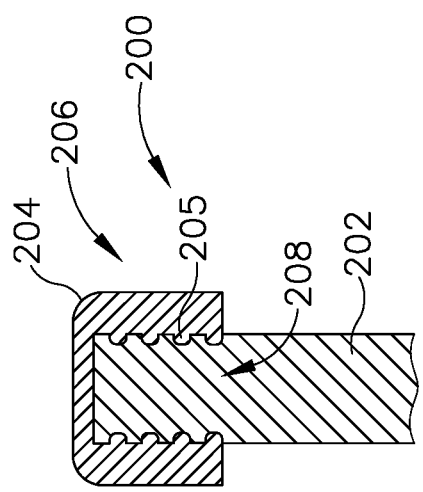
FIG. 20 depicts a cross-sectional side view of a portion of an alternative link that may be readily incorporated into the sphincter augmentation device of FIG. 3.
Figure 21:
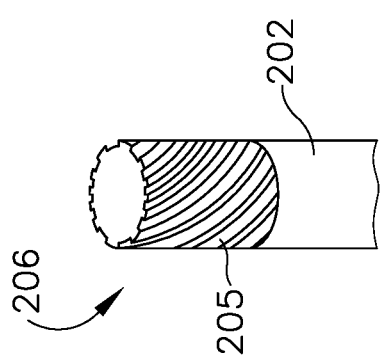
FIG. 21 depicts a perspective view of a portion of a wire of the alternative link of FIG. 20.

FIGS. 18-19 show alternative housings (180, 190) that may be readily incorporated into beads (30, 150) described above. Housings (180, 190) are substantially similar to housings (32, 34, 152, 154, 170) described above, with difference elaborated below. In particular, housing (180) defines opening (182) dimensioned to slidably contain wire (162), while housing (190) defines opening (192) dimensioned to slidably contain wire (162). Opening (182) includes a chamfered perimeter (184), while opening (192) includes a radiused perimeter (194). Chamfered perimeter (184) or radiused perimeter (194) may improve the contact between wire (162) and opening (182, 192) by allowing wire (162) to pivot relative to housing (180, 190). In some instances, the improved contact between wire (162) and opening (182, 192) may reduce the potential damage between opening (182, 192) and wire (162) as wire (162) moves relative to opening (182, 192). Chamfered perimeter (184) and radiused perimeter (194) may also help promote pivoting of wire (162) relative to housings (180, 190) in the expanded state, similar to angle (177) described above.

B. Features for Improved Link Strength

In some instances, links (40) may experience high external forces, such as when device (20) is exposed to an MRI, such as magnetic forces of 1.5 tesla and above. If external forces are great enough and aligned with link (40), link (40) may be damaged. For example, ball tips (44) may be torn off of wire (42), or wire (42) may be bent or snapped. In other instances, links (40) may experience cyclical stress and fatigue on wires (42). For example, during a standard MRI scan, a varying magnetic field may cause magnets (60) to twist in a first direction and alternate back and forth in several directions with links (40) being the only apparatus preventing individual beads (30) from separating apart. Links (40) may be exposed to cyclic stresses leading to fatigue of wire (42). Therefore, it may be desirable to increase the strength of a links (40) to help prevent damage to links (40), by bending/breaking wires (42), removing ball tips (44) from wires (42), etc.

One point of potential weakness for links (40) is in the connection between the wire (42) and the ball tips (44), as ball tips (44) may be torn off of wire (42) under sufficient force. Therefore, it may be desirable to increase the strength of connection between ball tips (44) and wire (42). In some instances, it may be desirable to increase the strength of connection between ball tips (44) and wire (42) such that the connection is stronger than the shear strength of wire (42) itself. FIGS. 20-23 depict two different alternative links (200, 210) that may be readily incorporated into device (20) in replacement of links (40, 100, 110, 130, 160) described above. Links (200, 210) are substantially similar to links (40, 100, 110, 130, 160) described above, with differences elaborated below. Therefore, links (200, 210) may be used to slidably couple adjacent beads (30, 150) in accordance with the description above. Instead of ball tips (44), links (200, 210) include a threaded end cap (204) and an orbit formed end cap (214), respectively. Threaded end cap (204) and orbit formed end cap (214) may function substantially similar as ball tips (44), but with increased coupling strength to wire (202).

In particular, link (200) includes a wire (202) that terminates into terminating end (206). Terminating end (206) includes a knurled surface (205). Knurled surface (205) of terminating end (206) is dimensioned to receive threaded end cap (204). When coupled, threaded end cap (204) and knurled surface (205) may have improved coupling strength via the friction features between knurled surface (205) and threaded end cap (204) as compared to welding ball tips (44) with wire (42). In other words, if threaded end cap (204) is pulled away from wire (202) with an increased tension force, threaded end cap (204) may remain associated with knurled surface (205). Threaded end cap (204) may be made of a harder material than wire (202) such that cap (204) may help create a pattern on wire (202) when coupling each other, thereby helping interlock cap (204) with wire (202).

Link (210) includes a wire (212) and an orbit formed end cap (214). Obit formed end cap (214) may be attached to wire (212) by rotating and orbiting cap (214) and introducing cap (214) to wire (212). The movement of orbiting cap (214) as wire (212) is introduced forms/smears the metal, thereby attaching cap (214) to wire (212). While welding pulls the hardness out of the wire due to a head effected zone, the orbiting method of attaching cap (214) to wire (212) maintains the hardness and tensile properties of the metal. This coupling may improve the coupling strength in tension as compared to welding ball tips (44) with wire (42).

Figure 24:
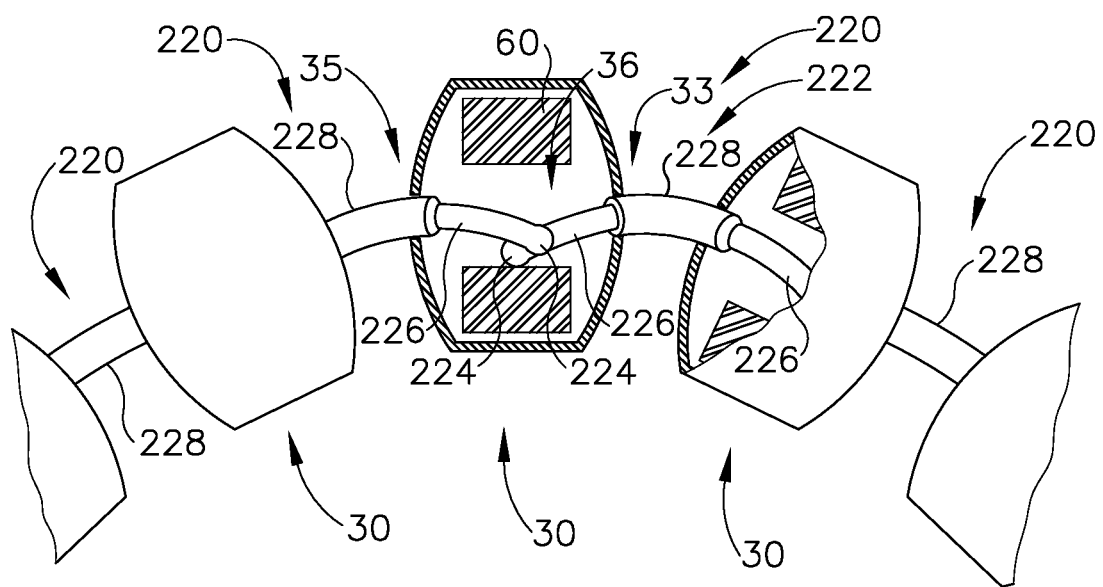
FIG. 24 depicts a top plan view of beads of FIG. 6 connected by a plurality of alternative links, with selected portions of bead casings cut away to reveal internal structures.
Figure 25:
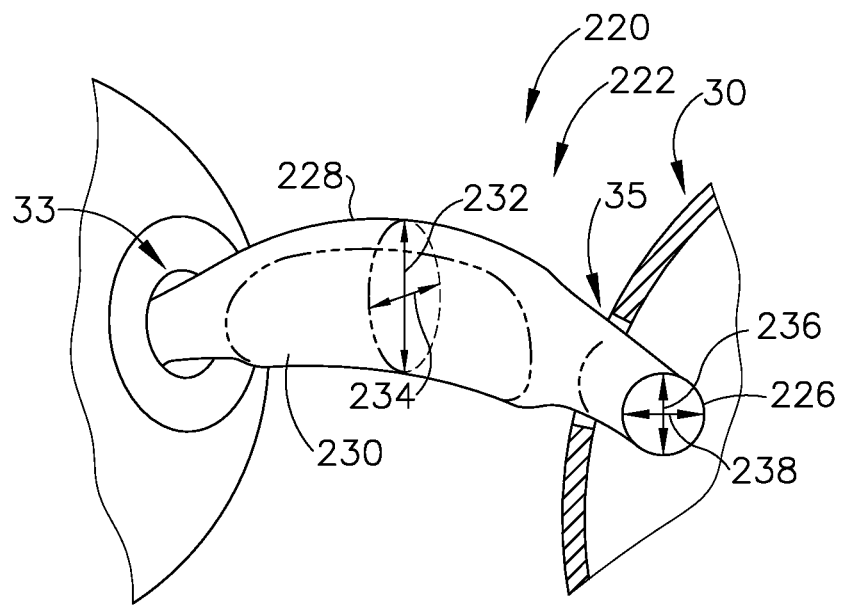
FIG. 25 depicts a partial perspective view of the beads and a link of FIG. 24, with selected portions of a bead casing and a link cut away to reveal internal structures.

In some instances, it may be desirable to change the cross-section of wire (42) in order to provide a higher moment of inertia in one direction, compared to another direction. FIGS. 24-25 show another alternative link (220) that may be readily incorporated into device (20) in replacement of links (40, 100, 110, 130, 160, 200, 210). Link (220) includes an elongated arched body (222) terminating into ball tips (224). Arched body (222) includes a central exterior portion (228) and two chamber portions (226). Chamber portions (226) are dimensioned to be slidably housed within chamber (36) of bead (30), while exterior portion (228) may not be configured to enter within chamber (36). However, this is merely optional, as in some instances, such as where bead (30) has non-circular openings similar to openings (174) described above, exterior portion (228) may enter chamber (36).

In the current example, chamber portions (226) have an aspect ratio of 1:1. In other words, chamber portions (226) have equal cross-sectional height (236) and width (238) dimensions. However, exterior portion (228) has a pair of flattened surfaces (230) such that the aspect ratio of exterior portion (228) is not 1:1. In the current example, exterior portion (228) has a larger height (232) than width (234). With the change in cross-sectional aspect ratio, the moment of inertia is increased in one direction, and decreased in another. This change in moment of inertia may be strategically used to allow links (220) to be stronger in one direction of force, as compared to another direction. This variable cross-section may help provide increased stiffness of links (220), especially during an MRI.

Figure 27:
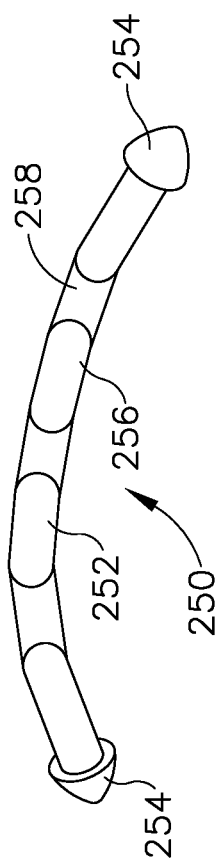
FIG. 27 depicts a perspective view of an alternative link that may be readily incorporated into the sphincter augmentation device of FIG. 3.
Figure 28:
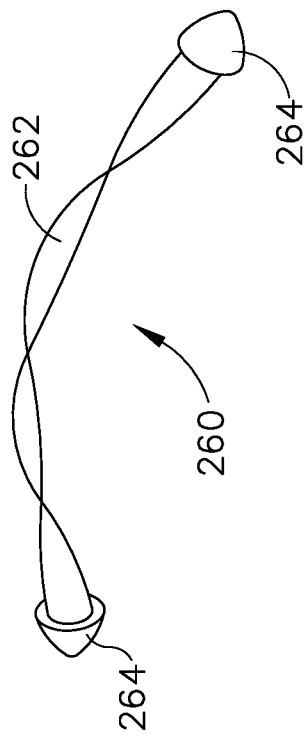
FIG. 28 depicts a perspective view of an alternative link that may be readily incorporated into the sphincter augmentation device of FIG. 3.
Figure 26:
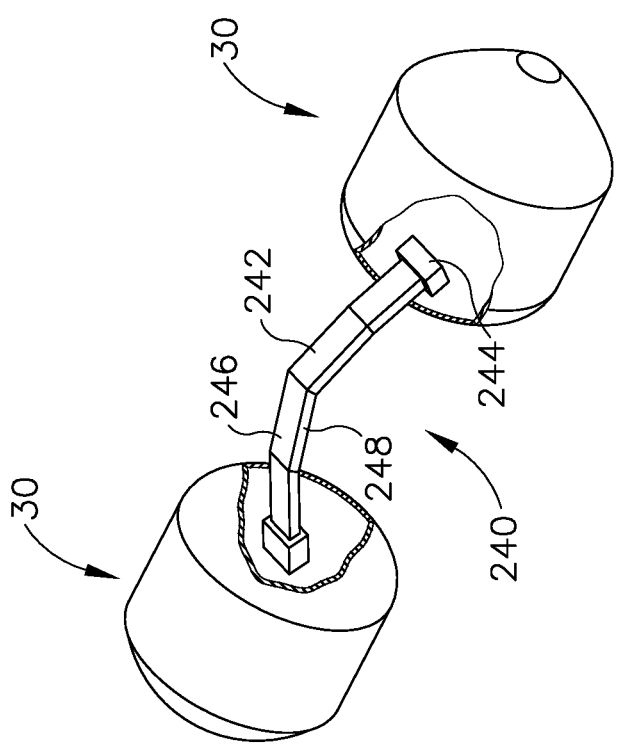
FIG. 26 depicts a partial perspective view of the beads of FIG. 6 connected by an alternative link, with selected portions of the bead casings cut away to reveal internal structures.

FIGS. 26-28 show various other links (240, 250, 260) that have different geometries to help increase strength and/or flexibility. FIG. 26 shows link (240) including rolled wire (242) and tips (244), which may function substantially similar to wire (42) and ball tips (44) described above, with differences elaborated below. Rolled wire (242) includes flat surfaces (246, 248) formed when wire (242) is rolled. Flat surfaces (246, 248) also help change the aspect ratio, thereby changing the moment of inertia in similar fashion to wire (212) described above. Rolled wire (242) may also increase the yield strength of link (240).

FIG. 27 shows link (250) that includes wire (252) and ball tips (254), which may function substantially similar to wire (42) and ball tips (44) described above, with differences elaborated below. While wire (242) has continuous flat surfaces (246, 248) extending between ball tips (244), wire (252) includes a linear pattern of circular portions (256) separated by flattened portions (258). Flattened portions (258) may not only provide the benefits associated with changing the moment of inertia; but may also vary in length and angular orientation about the longitudinal axis of wire (242). These deviations may improve the stiffness of wire (242) to bending in different planes.

FIG. 28 shows link (260) that includes wire (262) and ball tips (264), which may function substantially similar to wire (42) and ball tips (44) described above, with differences elaborated below. Wire (262) is a spiral wire such that the moment of inertia from a particular plane changes continuously along the length of wire (262). The change in moment of inertia may provide various advantages, similar to those described above.

In some instances, it may be desirable to have a wire (42, 102, 112, 132, 162, 202, 212, 222, 242, 252, 262) formed out of a plurality of stranded or braided wires. This may provide higher flexibility than a solid wire of the same cross-sectional area. The greater flexibility reduced the stress of wire (42, 102, 112, 132, 162, 202, 212, 222, 242, 252, 262) during movement. The more individual wire strands in a bundle, the more flexible, kink-resistant, break-resistant, and stronger the wire (42, 102, 112, 132, 162, 202, 212, 222, 242, 252, 262) becomes. The braided wire could be made of a single, larger central strand or bundle, with surrounding wires of smaller diameter wrapped or braided around the central stiffer core. This would allow the wire to act as a solid wire would during expansion and contraction of device, but also allow the wire more flex resistance, tensile strength, and shear head strength. In instances where wire (202) is formed of braided wire, end cap (204) may twist together with braids and interlock such that wire (202) would not need a spiral or radial pattern to interlock.

In some instance, it may be desirable to work harden wire (42) to increase the twist resistance strength. Wires (42) could be cold worked, thereby increasing the tensile strength of wire (42). In such instances, wire (42) may originally be 0.002-0.004 inches larger in diameter than needed, and then cold rolled down to the desired diameter.

In some instances, it may be desirable to make wire (42) out of a Nickel Titanium alloy, such as Nitinol. The hyperelastic properties of nitinol would limit the fatiguing of the wire as it is exposed to repeated twisting.

III. Exemplary Sphincter Augmentation Devices with Improved Bead Casing for Uniformity, Control, And Strength As mentioned above, beads (30) are formed from two housings (32, 34) that are coupled together when magnets (60) and links (40) are suitably attached. Housing (32, 34) may be coupled via a welding process. In some instances, it may be desirable to ensure magnets (60) are properly placed within housings (32, 34) to better control the magnetic field generated by an assembled device (20). In some instances, it may be desirable to make sure housings (32, 34) are suitably aligned with each other prior to being coupled. It may also be desirable to ensure the quality of weld coupling housing (32, 34) is of high integrity. The following are features that may improve the coupling of housings (32, 34) by ensuring control in uniform beads and bead strength.

Figure 29:
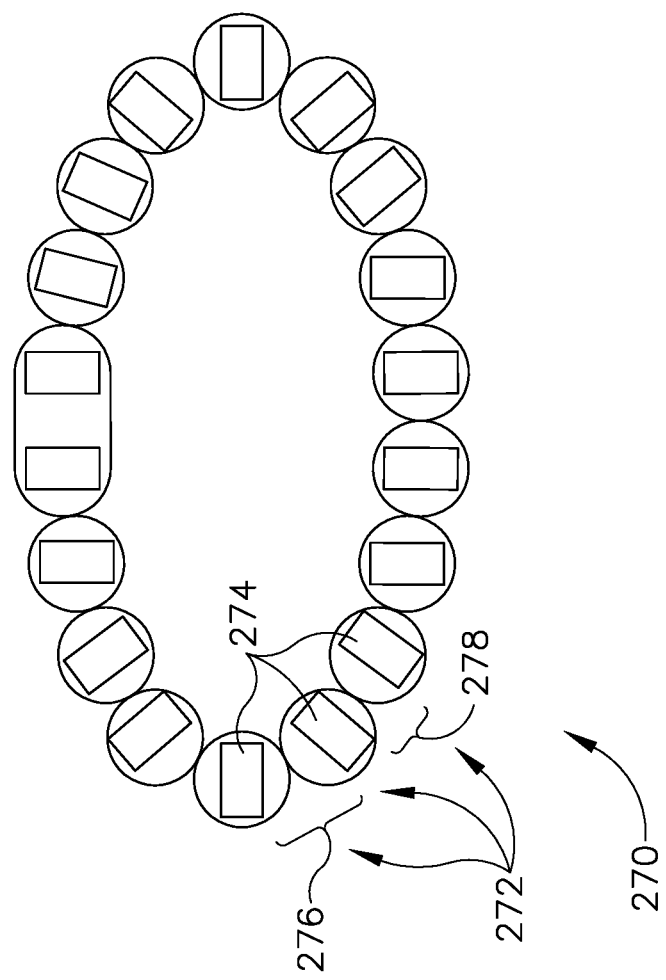
FIG. 29 depicts a top plan view of an alternative sphincter augmentation device, with selected portions of bead casings cut away to reveal internal structures.

FIG. 29 shows an exemplary alternative device (270) that may be used in replacement of device (20) described above. Device (270) is substantially similar to device (20) described above, with differences elaborated below. Device (270) includes a plurality of beads (272), each housing a magnet (274). Beads (272) are connected by links (not shown) similar to links (40, 100, 110, 130, 160, 200, 210, 220, 240, 250, 260) described above. However, magnets (274) are strategically placed within beads (272) to be closer to a first adjacent bead (272) as compared to a second adjacent bead (272). In other words, magnet (60) in one adjacent bead (272) may be spaced a first distance (278) from center bead (272), while magnet (60) in the second adjacent bead (272) may be spaced a second, longer, distance (276). This may allow for better control of the profile of device (270) in the contracted state (as shown in FIG. 29). For instance, device (270) may have a substantially oval profile compared to a substantially circular profile. Therefore, it may be important to properly place magnet (60) within bead (272).

Figure 30:
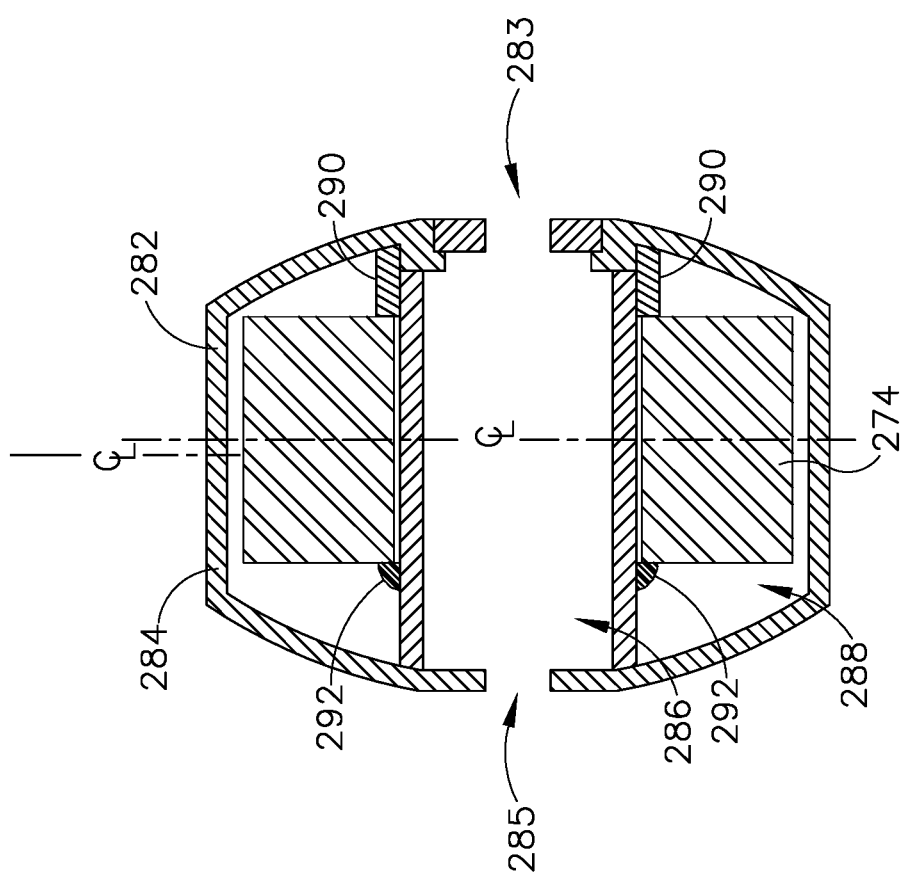
FIG. 30 depicts a cross-sectional front view of a bead and magnet of the alternative sphincter augmentation device of FIG. 29.

As best seen in FIG. 30, bead (272) includes two housings (282, 284) that define an opening (283, 285) and a chamber (286); which may be substantially similar to housings (32, 34) and opening (33, 35) and chamber (36) described above, respectively. Additionally, housings (282, 284) define a magnetic chamber (288) that is isolated from chamber (36) when housings (282, 284) are assembled. One housing (282) includes a magnet position shoulder (290). With magnet (60) abutting against magnet position shoulder (290), the other end of magnet (60) may be attached to the interior of a housing (282, 284) via an epoxy fixation element (292). Epoxy fixation element (292) may fix magnet (60) to housing (282). Magnet (60) may be rotationally and translatably fixed relative to housing (282) once epoxy fixation element (292) is suitably deployed and dried. Magnet position shoulder (290) is dimensioned to abut against an end of magnet (60) in order to accurately and precisely control the positioning of magnet (60) within magnetic chamber (288) when bead (272) is being assembled. The location of position shoulder (290) may be determinate of the end position of magnet (60). Position shoulder (290) may include a titanium coating to help accurately determine the final resting position of magnet (60). Accurate placement of magnet (60) within bead (272) may allow for more accurate control of distances (276, 278) when device (20) is assembled.

While epoxy is used to fix magnet (60) in the current example, any other suitably fixation means may be utilized as would be apparent to one having ordinary skill in the art in view of the teachings here. For example, magnet (60) may couple with housings (282, 284) via a frictionally pressed interference fit. While in the current example, one magnetic position shoulder (290) is used, a radial array of magnet position shoulders (290) may be used, a single annular magnetic position shoulder (290) may be used, or any other suitable arrangement of magnetic position shoulders (290) may be used as would be apparent to one having ordinary skill in the art in view of the teachings herein.

As mentioned above, it may be desirable to make sure housings (32, 34) are suitably aligned with each other prior to being coupled. FIGS. 31-33 show an exemplary alternative bead (300) that is configured to suitably orient housings (302, 304) relative to each other during assembly. Bead (300) may be substantially similar to bead (30, 150, 272) described above, with differences elaborated below. Therefore, housings (302, 304) are substantially similar to housings (32, 34) described above, with differences elaborated below. Together, housings (302, 304) include an alignment coupling assembly (305) configured to suitably orient housings (302, 304) relative to each other during assembly. Alignment coupling assembly (305) includes an array of protrusions (308) defining recesses (306) on first housing, and a complementary array of protrusions (312) defining recesses (310) on second housing (304). Protrusions (308, 312) and recesses (306, 310) are complementary such that protrusions (308) of housing (302) are dimensioned to fit within recesses (310) of housing (304), and protrusions (312) of housing (304) are dimensioned to fit within recesses (306) of housing (302). As best shown in FIG. 33, protrusions (308, 312) are not arranged around the circumference of housings (302, 304) in equal angular spacing. Therefore, housings (302, 304) may only align to suitably couple when angularly oriented relative to each other in one, specific, orientation. Once suitably coupled, housings (302, 304) may be fixed to each other via welding of weld lines (307).

Figure 34:
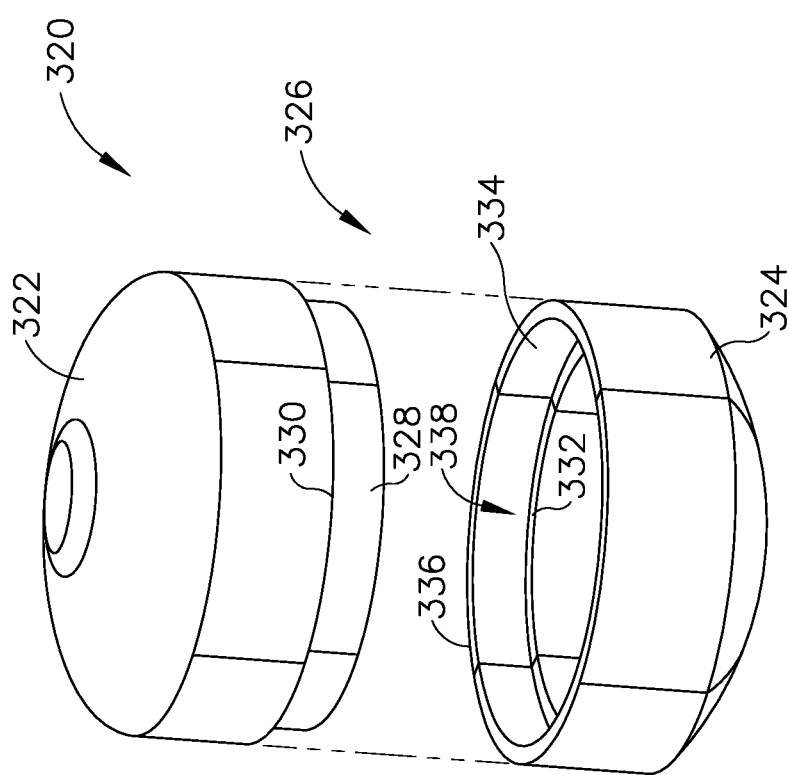
FIG. 34 depicts an exploded perspective view of an alternative bead that may be readily incorporated into the sphincter augmentation device of FIG. 3.
Figure 35:
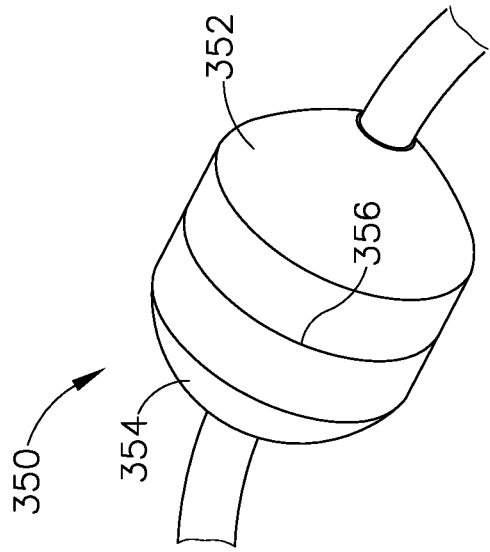
FIG. 35 depicts a perspective view of an alternative bead that may be readily incorporated into the sphincter augmentation device of FIG. 3.

As mentioned above, it may also be desirable to ensure the quality of weld coupling housing (32, 34) is of high integrity. FIG. 34 shows an alternative bead (320) having a predefined weld path with overlapping features to tolerate higher heat without collateral damage to housings (322, 324). Bead (320) may be substantially similar to bead (30, 150, 272, 320) described above, with differences elaborated below. Therefore, housings (322, 324) are substantially similar to housings (32, 34) described above, with differences elaborated below. Housings (322, 324) of bead (320) together form a coupling assembly (326). Coupling assembly (326) includes an interior sleeve (328) and a shoulder (330) of housing (322); and an interior shoulder (332), an interior surface (334), a shoulder (336) of second housing (324) defining a recess (338). Recess (338) is dimensioned to receive interior sleeve (328) such that interior sleeve (328) rests against interior shoulder (332) of second housing (324). Additionally, shoulder (330) of first housing (322) is dimensioned to rest against shoulder (336) of second housing (324) when housings (322, 324) are assembled. The overlapping nature of sleeve (328) within recess (338) could be used to align and nest the two housings (322, 324) and create a continuous weld path. The weld could be a spiral pattern starting at the position where shoulders (330, 336) touch. An alternative would be to start with a circumferential seam that has one vertical standing feature and a mating receding feature that enable the weld to go around the bead, up the side to the pole and around the pole in one continuous laser weld.

Figure 39:
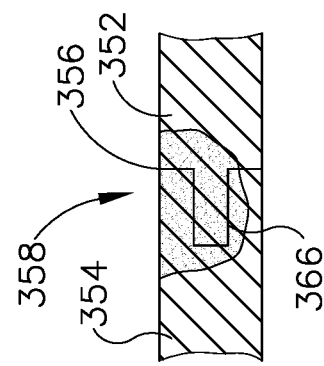
FIG. 39 depicts an alternative coupling configuration between housings of the bead of FIG. 35.
Figure 38:
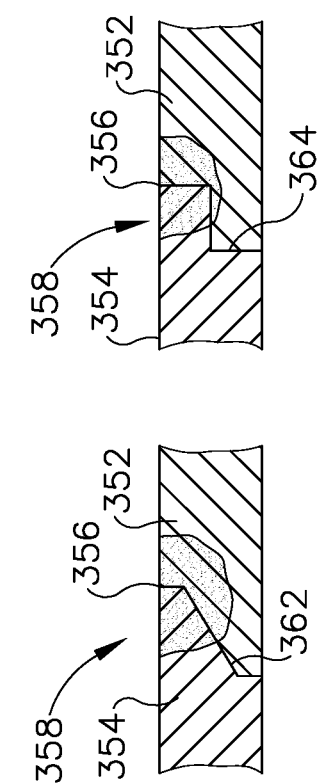
FIG. 38 depicts an alternative coupling configuration between housings of the bead of FIG. 35.
Figure 37:
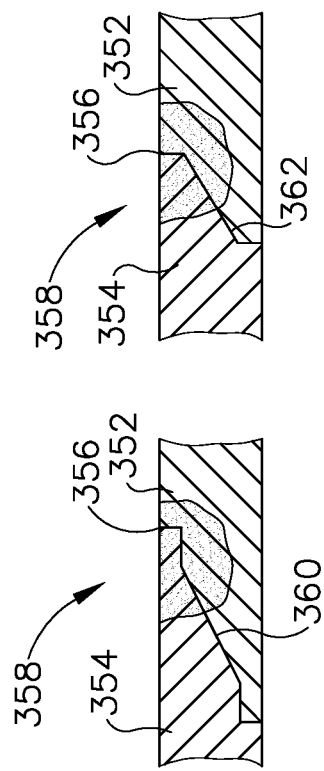
FIG. 37 depicts an alternative coupling configuration between housings of the bead of FIG. 35.
Figure 36:
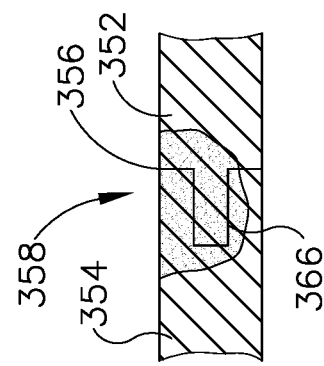
FIG. 36 depicts an alternative coupling configuration between housings of the bead of FIG. 35.

FIGS. 35-39 show an alternative bead (350) having housings (352, 354) connected together at a weld lines (356), where FIGS. 36-39 show various connecting geometries used to couple housings (352, 354) is facilitation of welding. FIG. 36 shows housings (352, 354) having an overlapping lip joint coupling profile (360). FIG. 37 shows housings (352, 354) having a lead-in joint coupling profile (362). FIG. 38 shows housings (352, 354) having a step coupling profile (364). FIG. 39 shows housings (352, 354) having a tongue and groove coupling profile (366). Each profile has an overlapping nature around the perimeter of the weld areas. A laser could be used to fuse this overlapping area rather than trying to create a butt weld. This would additionally improve the alignment of the housings (352, 354). Additionally, these coupling profiles could be thin enough and have a lead in where the two housings (352, 354) could be press fit together, creating a more compacted joint which would produce a better weld without any filler material.

It may be desirable to have improved micro surface chemical composition and crystallization on a weld combining two housings (352, 354). Limiting oxygen exposure during the welding operation may prevent the introductions of oxides into the weld itself, creating better corrosion resistance. This can be done by introducing an argon or helium shield gas to protect the housings (352, 354). This could be detected in the final product by sectioning the weld and examining it for oxides formed within the weld pool. This may dramatically increase the strength of the weld and its resistance to acids and corrosion. An alternative to the shield gas could be the welding of the system within a vacuum. The weld could be created by electron beam laser. Pulsed beam or continuous beam welding is possible, but pulsed beam welding may minimize the heat-affected zone adjacent to the welded area and prevent warpage of the parts that might otherwise be caused by continuous beam welding. The pulsing could be on the order of 10-1000 Hz.

Controlled thermal oxidation of the titanium after welding may create a crystallinity of the surface layer of the bead, creating an improved integration or prevention of integration into the surrounding tissues when device (20) is implanted. The properties of the surface oxide may influence the biocompatibility of titanium. Titanium may contain a thin amorphous layer that is naturally oxidized upon exposure to the atmosphere. Such a layer may have a thickness of 3-7 nm and a main component of stable $TiO_2$. With thermal oxidation treatment, the thickness of the oxide layer may be significantly increased. The crystallinity of this surface layer of titanium oxide may be significantly changed and may be composed of anatase and rutile crystal phases. An anatase film may attract calcium and phosphate ions from the physiological environment to form an apatite coating. Surface wettability is believed to be part of surface in the bioactivity of the titanium. The contact angles on the thermal-oxidation-treated titanium surfaces may be significantly lower than on a control plate; and a prolonged heat-treatment time may gradually decrease the contact angle. This may increase the wettability of the surface.

The laser itself may tend to influence the surface chemical properties and either reinforce the desired layered oxidation or interfere with it. With the correct gas mixture and the maintenance of temperature, the layers could result in $TiO_3$, TiO, or $TiO_2$. The $TiO_2$ anatase and rutile surface as described above may affect numerous surface properties of the implant. If not correctly controlled, the laser weld may result in numerous $TiO_3$ and TiO interfaces in the uniformity of the surface. A pulsed laser may be controlled appropriately with a shielding inert gas to prevent oxidation until desired and at the desired temperature. In addition, aging treatments can control the grain shapes and grain boundaries of the welded zone, the refinement to the grain can lead to strengthening the weld zone and improve the joint.

All beads and links described herein may be manufactured utilizing metal injection molding. Alternatively, near net metal injection molding may be used to create the bead and links described herein. In near net metal injection molding, the part may be created with metal injection molding, but with extra material included. The extra material may be removed using conventional machining to finish the bead or link. Secondary forming could also be added to improve work hardening of the metal injection molded part, thereby improving strength and hardness of one area of the bead/link over other area. Additionally, beads and/or links may be created using 3D printing techniques.

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An implantable restriction device, the implantable restriction device comprising: (a) a plurality of beads, wherein each bead comprises: (i) a housing, (ii) a passageway extending through the housing, wherein the passageway defines an axis, and (iii) at least one magnet disposed around the passageway; (b) a plurality of links joining the beads together, wherein portions of the links are slidably disposed in corresponding passageways of the beads such that the plurality of beads are operable to transition between a constricted configuration and an expanded configuration; and (c) a parking feature configured to consistently position the at least one link relative to the housing in the contracted configuration.

Example 2

The implantable restriction device of Example 1, wherein each link in the plurality of links comprises more than one bend location.

Example 3

The implantable restriction device of Example 2, wherein the more than one bend location comprises a first portion of the link defining a first linear axis, a second portion of the link defining a second linear axis, and a third portion of the link defining a third linear axis, wherein the first linear axis, the second linear axis, and the third linear axis are not parallel relative to each other.

Example 4

The implantable restriction device of any one or more of Examples 1 through 3, wherein the parking feature is coupled with the at least one link, wherein the parking feature is configured to interact with a bead in the plurality of beads in order to consistently position the at least one link relative to the housing in the contracted state.

Example 5

The implantable restriction device of Example 4, wherein the parking feature comprises a spacer bead.

Example 6

The implantable restriction device of Example 5, wherein the spacer bead comprises a polymer.

Example 7

The implantable restriction device of Example 5, wherein the spacer bead is magnetized.

Example 8

The implantable restriction device of Example 5, wherein the spacer bead is configured to associate with a housing as the plurality of beads begin to transition from the contracted configuration toward the expanded configuration.

Example 9

The implantable restriction device of any one or more of Examples 4 through 8, wherein the parking feature comprises a magnetized tip.

Example 10

The implantable restriction device of any one or more of Examples 1 through 10, wherein the parking feature comprises a partitioning layer housed within the passageway.

Example 11

The implantable restriction device of Example 10, wherein the partitioning layer divided the passageway into two isolated chambers.

Example 12

The implantable restriction device of any one or more of Examples 1 through 11, wherein the link comprises a wire and two ball tips.

Example 13

The implantable restriction device of Example 12, wherein the ball tips are attached to the wire via a weld.

Example 14

The implantable restriction device of any one or more of Examples 1 through 13, wherein the link comprises a plurality of braided wires.

Example 15

The implantable restriction device of any one or more of Examples 1 through 14, wherein the link comprises a first cross-sectional area and a second cross-sectional area having different moment of inertias.

Example 16

The implantable restriction device of Example 15, wherein the first cross-sectional area comprises a flattened surface.

Example 17

An implantable restriction device, the implantable restriction device comprising: (a) a plurality of beads, wherein each bead comprises: (i) a housing, (ii) a passageway extending through the housing between a first orifice and a second orifice, wherein the passageway defines an axis, and (iii) at least one magnet disposed around the passageway; and (b) a plurality of links joining the beads together, wherein portions of the links are slidably disposed in corresponding passageways of the beads such that the plurality of beads are operable to transition between an constricted configuration and an expanded configuration, wherein the plurality of links are operable to pivot relative to the first orifice and the second orifice when the plurality of beads are in the expanded configuration.

Example 18

The implantable restriction device of Example 17, wherein the first orifice comprises a chamfered perimeter.

Example 19

The implantable restriction device of any one or more of Examples 17 through 18, wherein the first orifice comprises a non-circular profile.

Example 20

An implantable restriction device, the implantable restriction device comprising: (a) a plurality of beads, wherein each bead comprises: (i) a housing comprising a first piece and a second piece, (ii) a passageway extending through the housing, (iii) at least one magnet disposed around the passageway, and (iv) a coupling assembly configured to orient the first piece relative to the second piece when the first piece is initially coupled with the second piece; and (b) a plurality of links joining the beads together, wherein portions of the links are slidably disposed in corresponding passageways of the beads such that the plurality of beads are operable to transition between an constricted configuration and an expanded configuration.

V. Miscellaneous

It should also be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An implantable restriction device, the implantable restriction device comprising:
    (a) a plurality of beads, wherein each bead comprises:
        (i) a housing,
        (ii) a passageway extending through the housing, wherein the passageway defines an axis, and
        (iii) at least one magnet disposed around the passageway;
    (b) a plurality of links joining the beads together, wherein portions of the links are slidably disposed in corresponding passageways of the beads such that the plurality of beads are operable to transition between a constricted configuration and an expanded configuration; and
    (c) a parking feature configured to consistently position at least one link of the plurality of links relative to the housing in the contracted configuration, wherein the parking feature is coupled with the at least one link, wherein the parking feature is configured to interact with a bead in the plurality of beads in order to consistently position the at least one link relative to the housing in the contracted state.

2. The implantable restriction device of claim 1, wherein each link in the plurality of links comprises more than one bend location.

3. The implantable restriction device of claim 2, wherein the more than one bend location comprises a first portion of at least one of the links of the plurality of links defining a first linear axis, a second portion of the at least one of the links defining a second linear axis, and a third portion of the at least one of the links of the plurality of links defining a third linear axis, wherein the first linear axis, the second linear axis, and the third linear axis are not parallel relative to each other.

4. The implantable restriction device of claim 1, wherein the parking feature comprises a spacer bead.

5. The implantable restriction device of claim 4, wherein the spacer bead comprises a polymer.

6. The implantable restriction device of claim 4, wherein the spacer bead is magnetized.

7. The implantable restriction device of claim 4, wherein the spacer bead is configured to associate with a housing as the plurality of beads begin to transition from the contracted configuration toward the expanded configuration.

8. The implantable restriction device of claim 4, wherein the parking feature comprises a magnetized tip.

9. The implantable restriction device of claim 1, wherein the parking feature comprises a partitioning layer housed within the passageway.

10. The implantable restriction device of claim 9, wherein the partitioning layer divides the passageway into two isolated chambers.

11. The implantable restriction device of claim 1, wherein the at least one of the links of the plurality of links comprises a wire and two ball tips.

12. The implantable restriction device of claim 11, wherein the ball tips are attached to the wire via a weld.

13. The implantable restriction device of claim 1, wherein the at least one of the links of the plurality of links comprises a plurality of braided wires.

14. The implantable restriction device of claim 1, wherein the link comprises a first cross-sectional area and a second cross-sectional area having different moment of inertias.

15. The implantable restriction device of claim 14, wherein the first cross-sectional area comprises a flattened surface.

16. An implantable restriction device, the implantable restriction device comprising:
   (a) a plurality of beads, wherein each bead comprises:
      (i) a housing,
      (ii) a passageway extending through the housing between a first orifice and a second orifice, wherein the first orifice comprises a non-circular profile, wherein the passageway defines an axis, and
      (iii) at least one magnet disposed around the passageway; and
   (b) a plurality of links joining the beads together, wherein portions of the links are slidably disposed in corresponding passageways of the beads such that the plurality of beads are operable to transition between a constricted configuration and an expanded configuration, wherein the plurality of links are operable to pivot relative to the first orifice and the second orifice when the plurality of beads are in the expanded configuration.

17. The implantable restriction device of claim 16, wherein the first orifice comprises a chamfered perimeter.

18. An implantable restriction device, the implantable restriction device comprising:
   (a) a plurality of beads, wherein each bead comprises:
      (i) a housing,
      (ii) a passageway extending through the housing, wherein the passageway defines an axis, and
      (iii) at least one magnet disposed around the passageway;
   (b) a plurality of links joining the beads together, wherein portions of the links are slidably disposed in corresponding passageways of the beads such that the plurality of beads are operable to transition between a constricted configuration and an expanded configuration; and
   (c) a parking feature configured to consistently position at least one link of the plurality of links relative to the housing in the contracted configuration, wherein the parking feature comprises a partitioning layer housed within the passageway.

19. The implantable restriction device of claim 18, wherein the partitioning layer extends along a straight profile diagonally relative to the axis defined by the passageway.

20. The implantable restriction device of claim 18, wherein the housing defines a first opening and a second opening both in communication with the passageway, wherein the partitioning layer is located above the first opening and below the second opening.

* * * * *